(12) United States Patent
Cabib et al.

(10) Patent No.: US 9,958,328 B2
(45) Date of Patent: *May 1, 2018

(54) SINGLE DEVICE FOR GAS AND FLAME DETECTION, IMAGING AND MEASUREMENT, AND DRIFT CORRECTION METHOD THEREOF

(71) Applicant: CI SYSTEMS (ISRAEL) LTD., Migdal Ha'emek (IL)

(72) Inventors: Dario Cabib, Timrat (IL); Amir Gil, Kiryat Tivon (IL); Moshe Lavi, Nofit (IL); Liviu Singher, Kiryat Tivon (IL)

(73) Assignee: CI SYSTEMS (ISRAEL) LTD., Migdal Ha'emek (IL)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/551,599

(22) PCT Filed: Feb. 23, 2016

(86) PCT No.: PCT/IL2016/050204
§ 371 (c)(1),
(2) Date: Aug. 17, 2017

(87) PCT Pub. No.: WO2016/147169
PCT Pub. Date: Sep. 22, 2016

(65) Prior Publication Data
US 2018/0045567 A1    Feb. 15, 2018

Related U.S. Application Data

(63) Continuation-in-part of application No. 14/983,570, filed on Dec. 30, 2015, now Pat. No. 9,778,174.

(Continued)

(51) Int. Cl.
| | | |
|---|---|---|
| *G01J 3/28* | (2006.01) | |
| *G01J 3/02* | (2006.01) | |
| *G01N 21/3504* | (2014.01) | |

(52) U.S. Cl.
CPC ........... *G01J 3/2823* (2013.01); *G01J 3/0205* (2013.01); *G01J 3/2803* (2013.01); *G01N 21/3504* (2013.01); *G01N 2201/12* (2013.01)

(58) Field of Classification Search
CPC ...... G01J 3/0205; G01J 3/2803; G01J 3/2823; G01J 3/36; G01N 21/3504
See application file for complete search history.

(56) References Cited

U.S. PATENT DOCUMENTS

| | | |
|---|---|---|
| 4,081,207 A | 3/1978 | Dippel |
| 4,808,808 A | 2/1989 | Karasaki et al. |

(Continued)

FOREIGN PATENT DOCUMENTS

EP        0973019 A1 *  1/2000  ............. G01J 5/602

*Primary Examiner* — Mark R Gaworecki
(74) *Attorney, Agent, or Firm* — Mark M. Friedman

(57) ABSTRACT

Devices image radiation from a scene that includes two materials with spectral characteristics in two different wavelength regions. A lens forms an image of the scene on a detector that includes an array of elements. A filtering arrangement integrated with the detector allows half of the detector elements to detect radiation in one of the wavelength regions and the other half of the detector elements to detect radiation in the other wavelength region. Each detector element can be constructed from two different subelements that are sensitive to radiation in one of the respective wavelength regions. A blackbody source positioned within the devices reduces drift induced by changes to the environment surrounding the devices. The blackbody source projects radiation onto a region of the detector that does not receive radiation from the scene. Pixel signals produced (Continued)

from the scene radiation are modified based on pixel signals produced from the blackbody.

20 Claims, 20 Drawing Sheets

Related U.S. Application Data

(60) Provisional application No. 62/135,183, filed on Mar. 19, 2015.

(56) References Cited

U.S. PATENT DOCUMENTS

| | | | |
|---|---|---|---|
| 5,206,502 | A | 4/1993 | Gardner |
| 5,636,027 | A | 6/1997 | Spengler et al. |
| 5,784,507 | A | 7/1998 | Holm-Kennedy et al. |
| 8,049,163 | B1 | 11/2011 | Granneman et al. |
| 8,124,936 | B1 | 2/2012 | Lagna |
| 2001/0045516 | A1 | 11/2001 | Emanuel et al. |
| 2004/0075827 | A1 | 4/2004 | Byrne |
| 2004/0108564 | A1 | 6/2004 | Mitra |
| 2004/0149907 | A1 | 8/2004 | Vaidya |
| 2005/0263682 | A1 | 12/2005 | Eikenberry |
| 2006/0241495 | A1 | 10/2006 | Kurtz |
| 2007/0145310 | A1 | 6/2007 | Liang et al. |
| 2008/0210872 | A1 | 9/2008 | Grimberg |
| 2008/0251724 | A1 | 10/2008 | Baliga |
| 2010/0019154 | A1 | 1/2010 | Rafferty |
| 2014/0231650 | A1 | 8/2014 | Streuber et al. |

\* cited by examiner

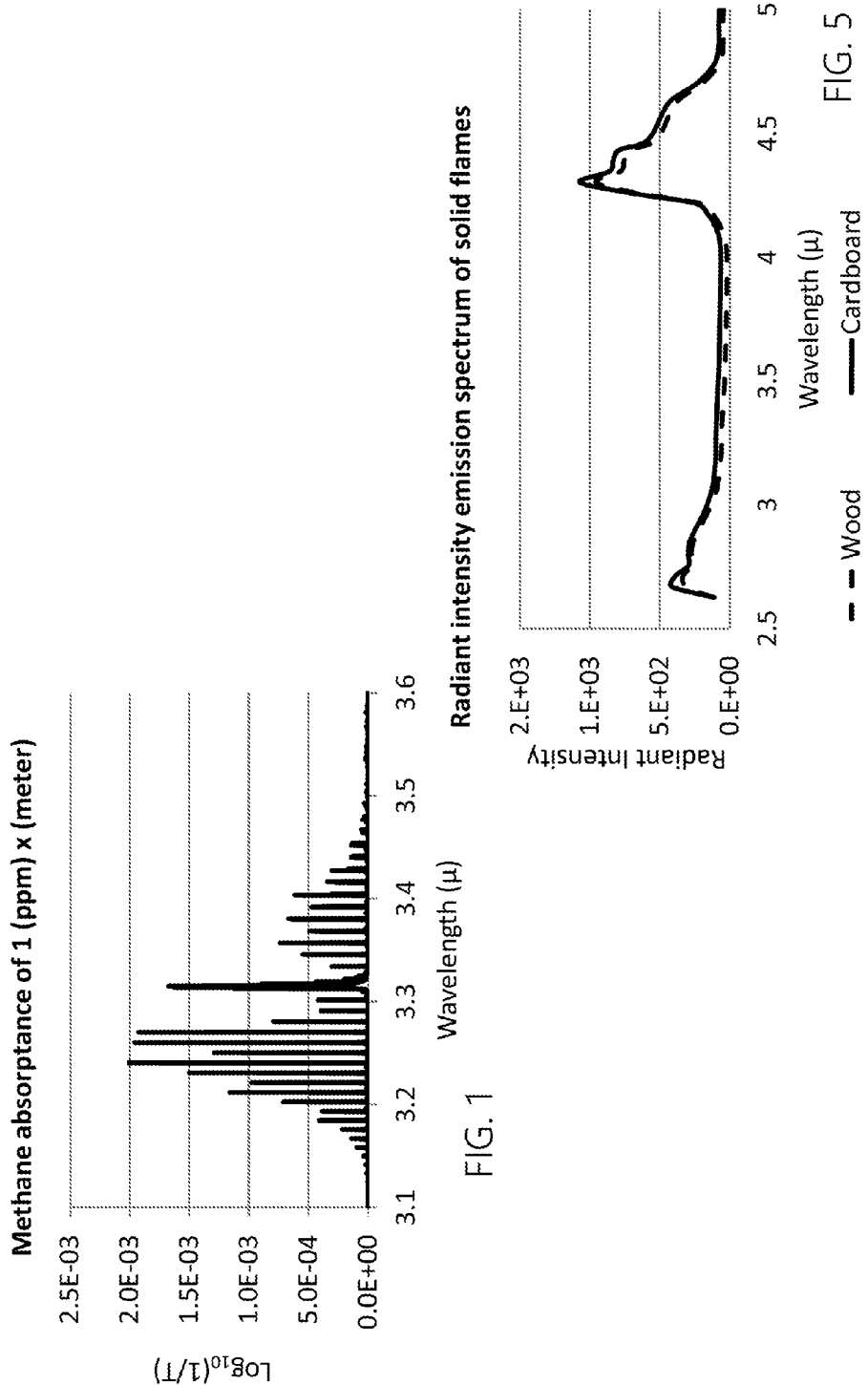

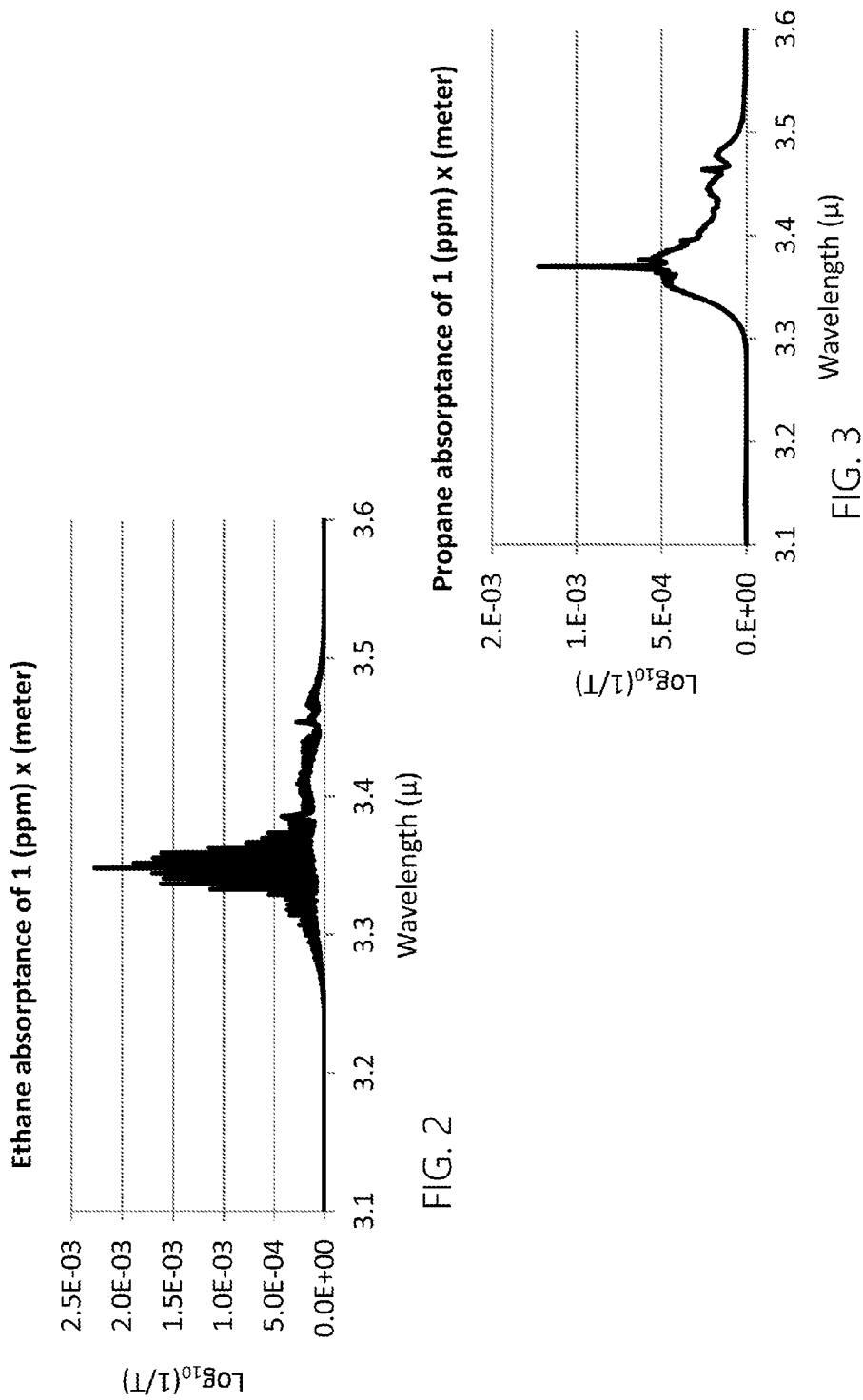

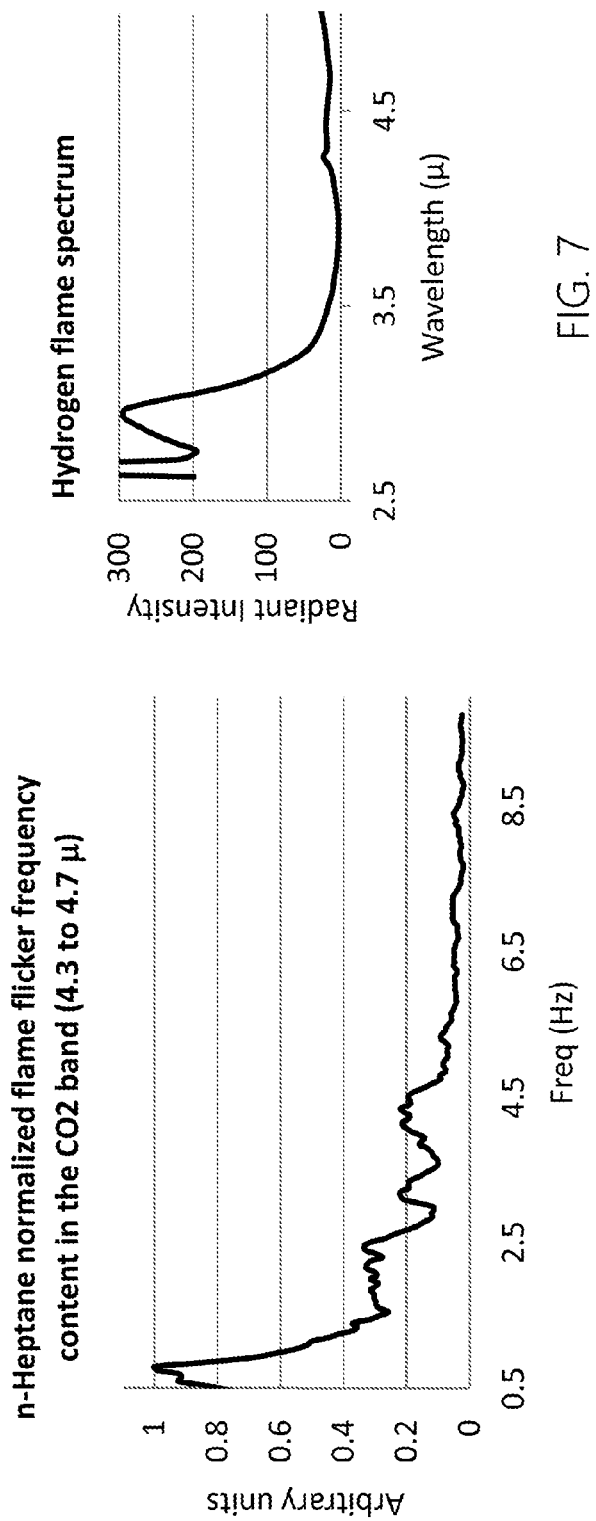

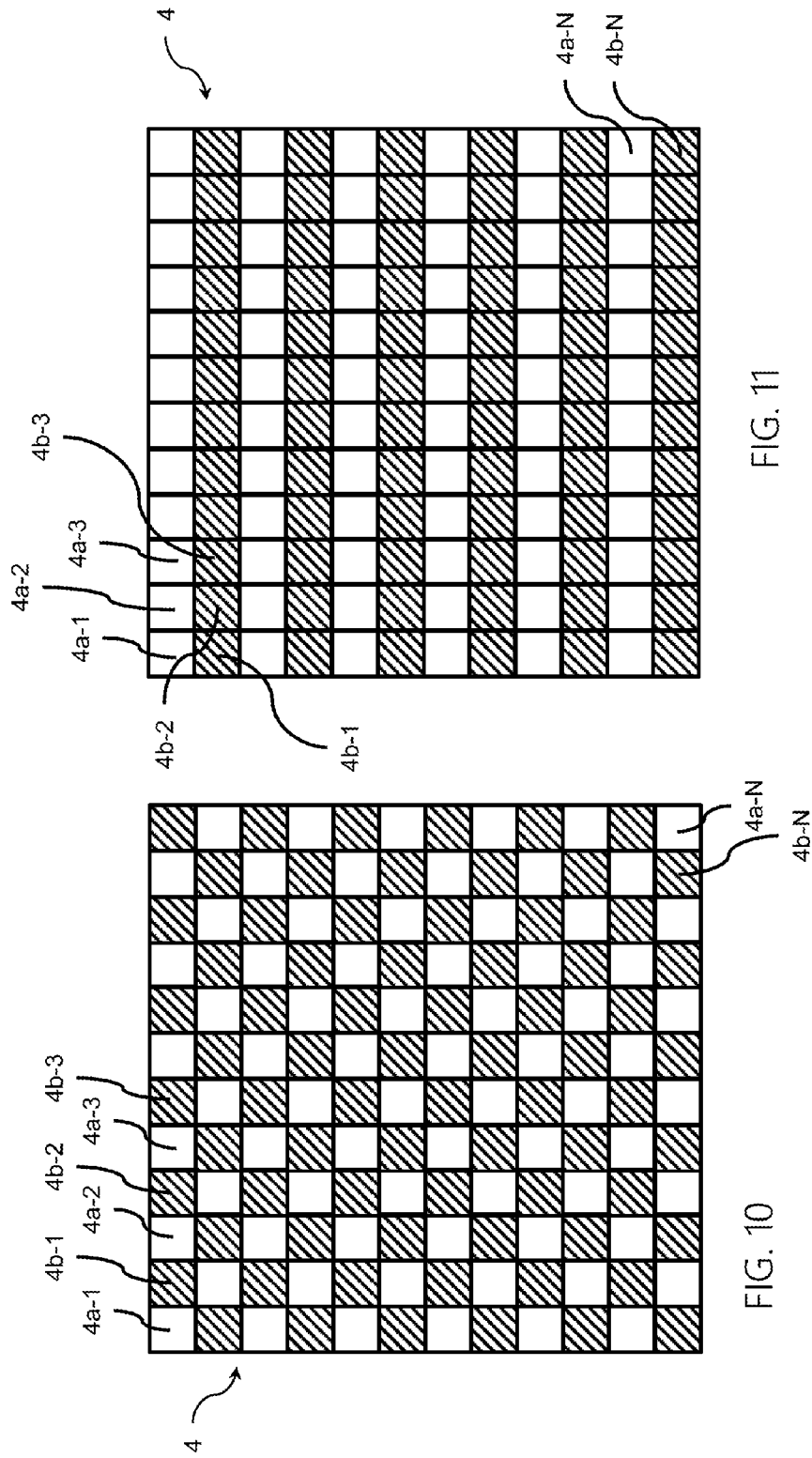

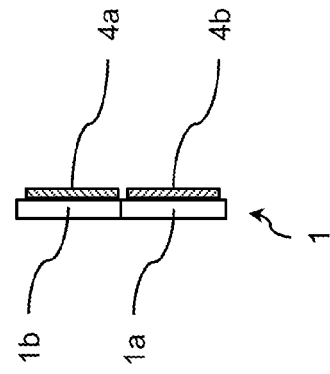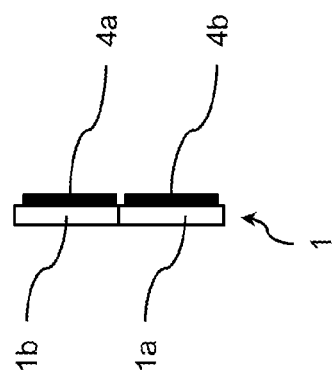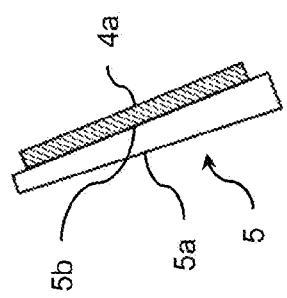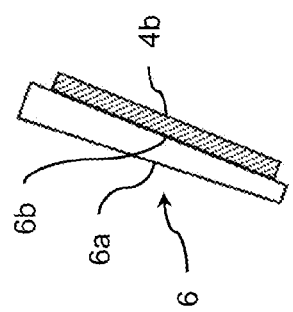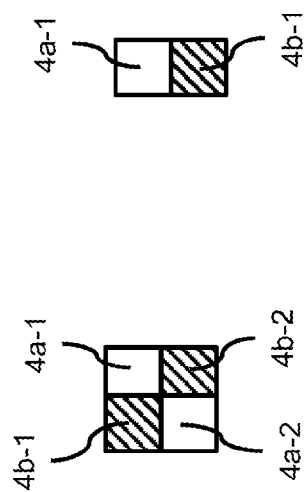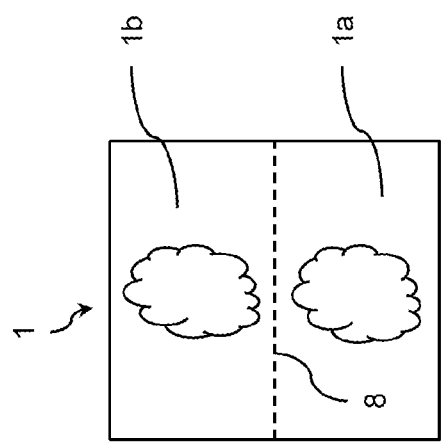

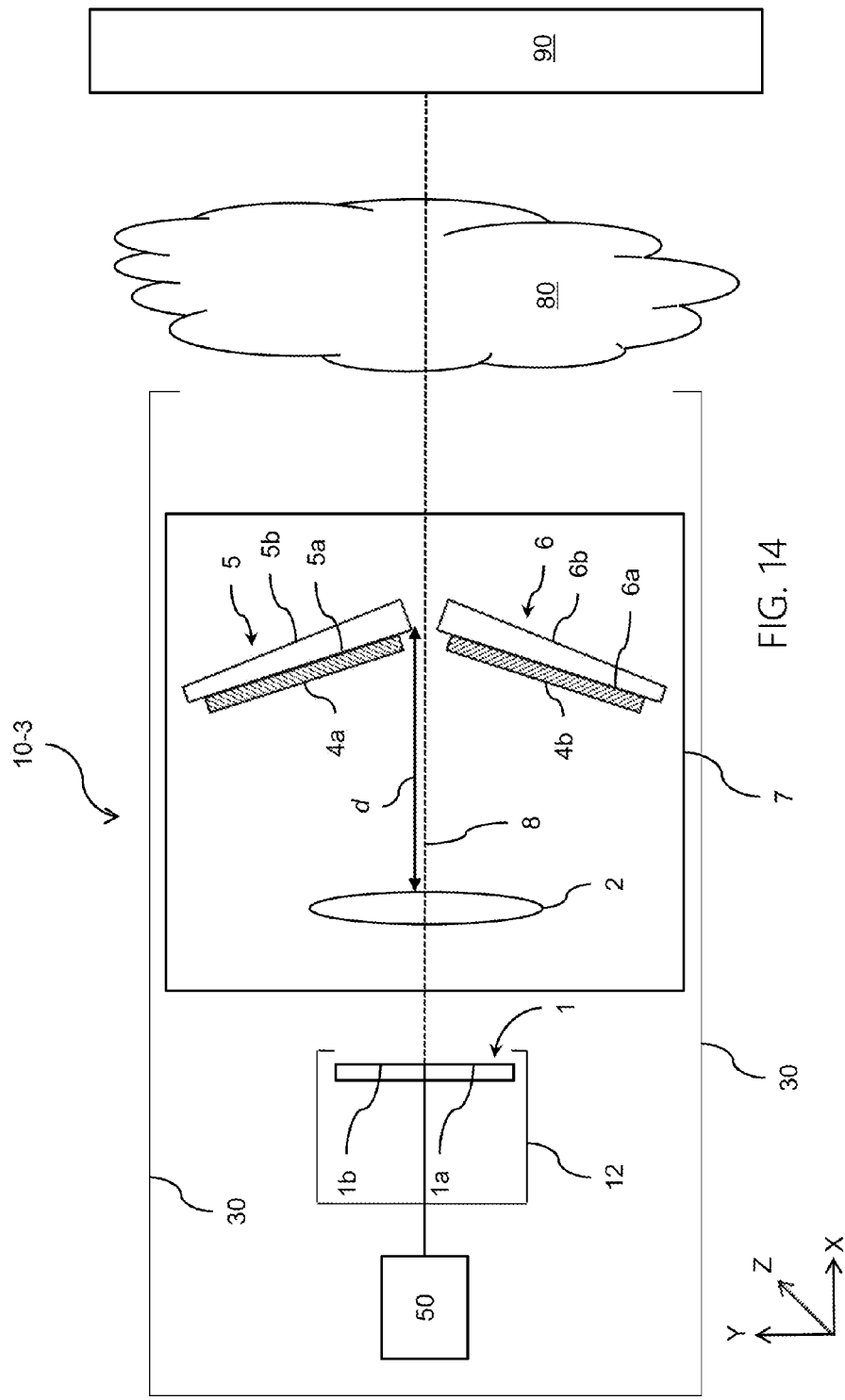

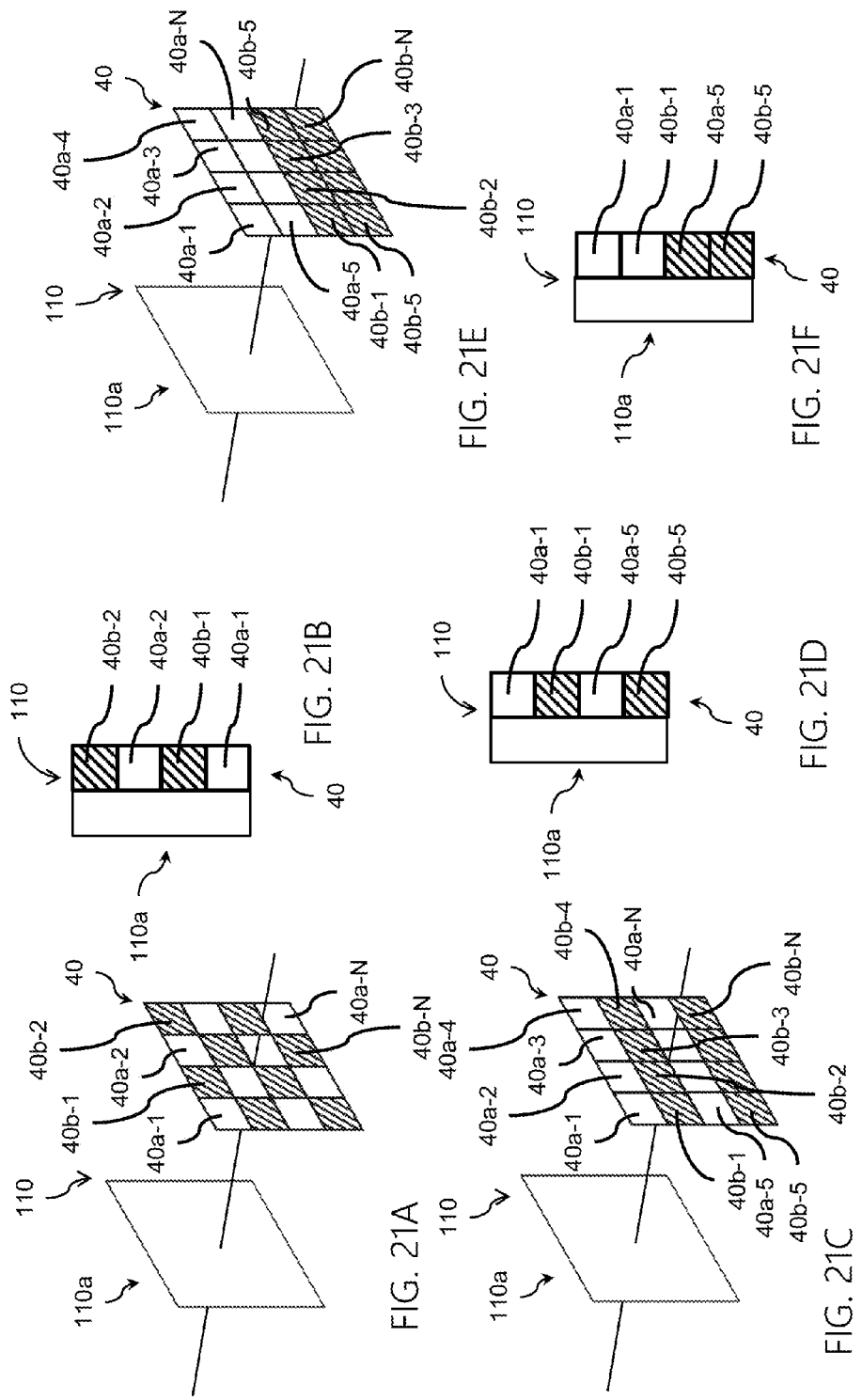

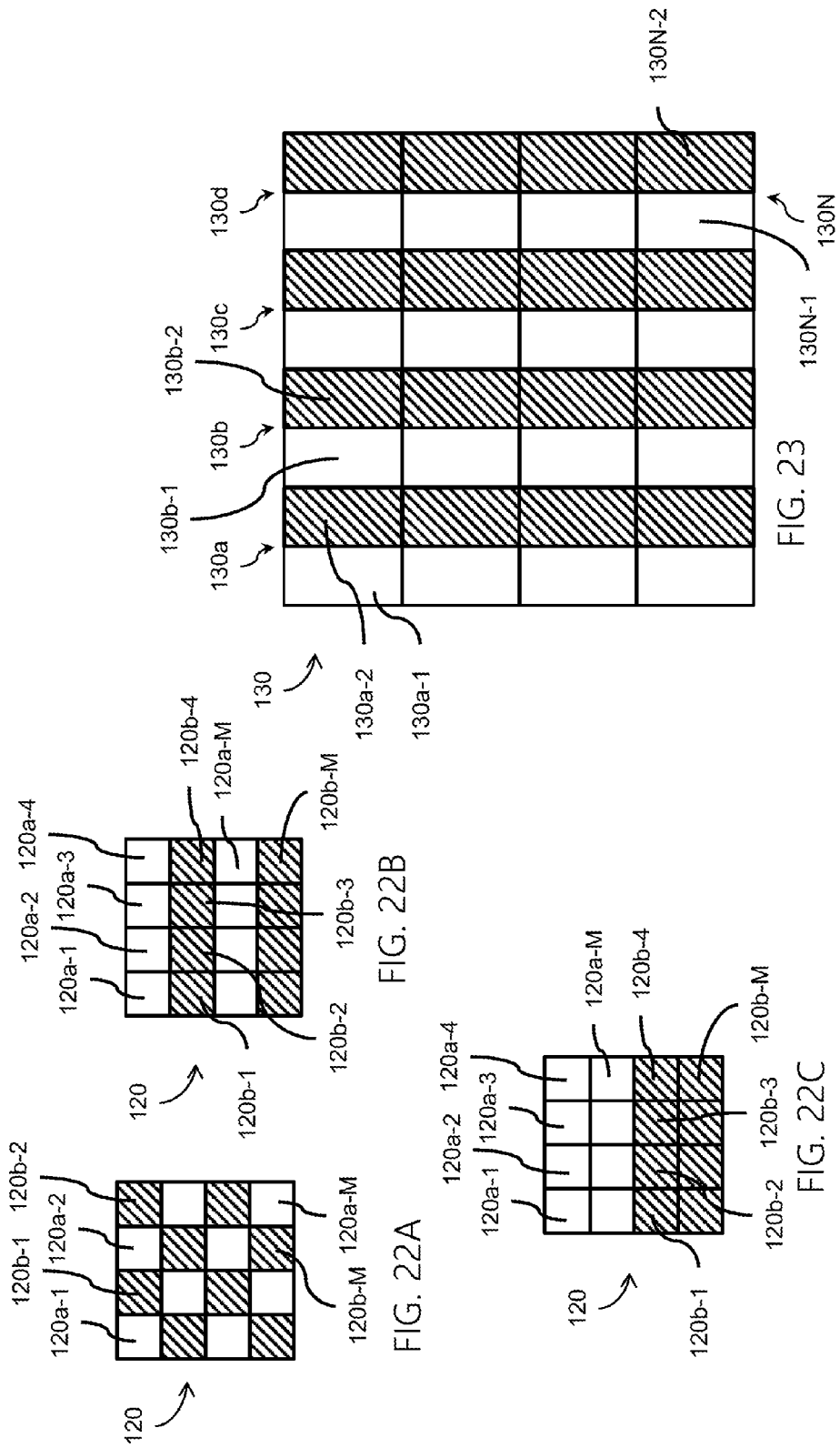

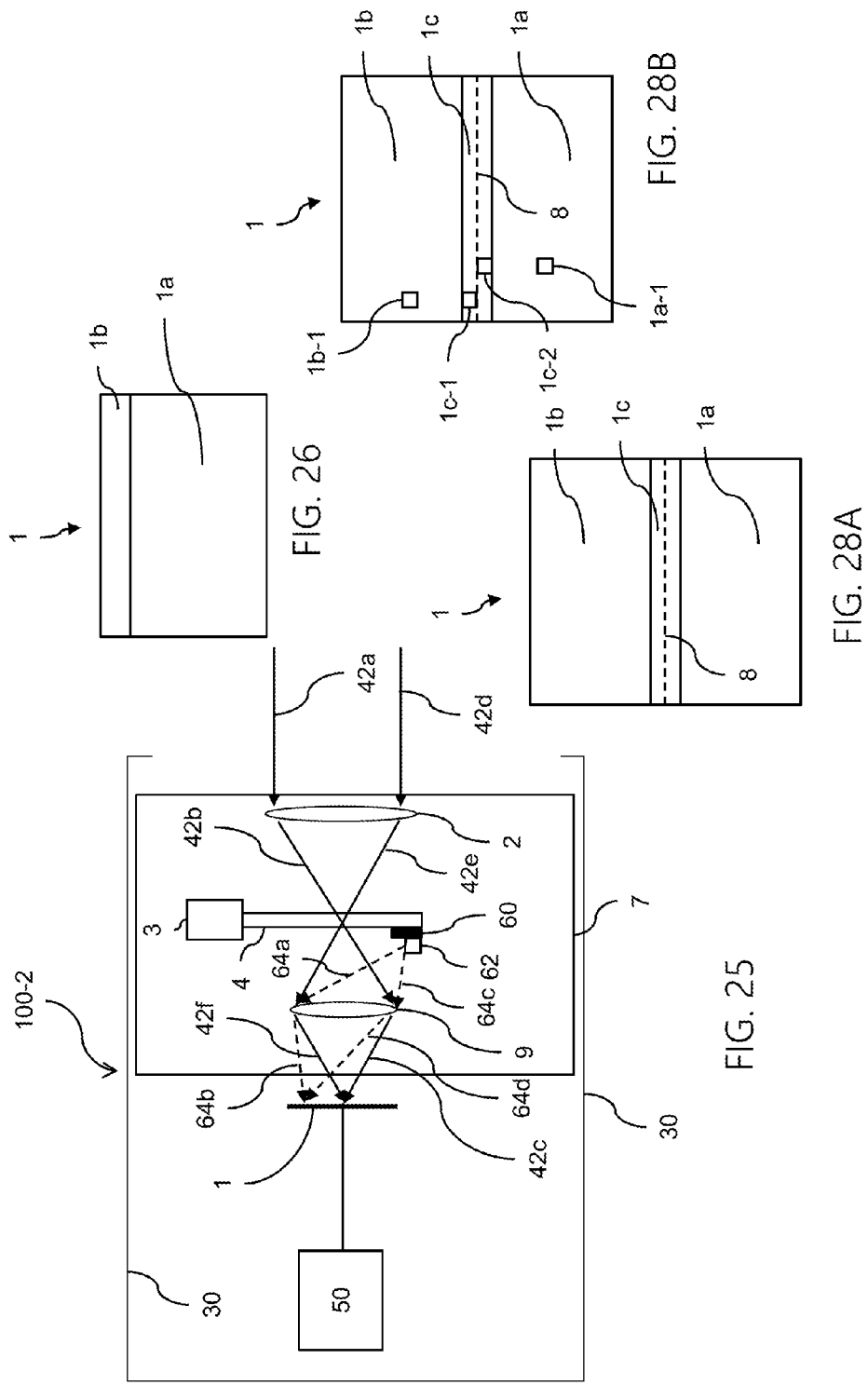

SINGLE DEVICE FOR GAS AND FLAME DETECTION, IMAGING AND MEASUREMENT, AND DRIFT CORRECTION METHOD THEREOF

CROSS-REFERENCE TO RELATED APPLICATIONS

This application is a Continuation-in-part of U.S. patent application Ser. No. 14/983,570 (now issued as U.S. Pat. No. 9,778,174), filed on Dec. 30, 2015. This application claims priority from U.S. Provisional Patent Application No. 62/135,183, filed Mar. 19, 2015. This application is related to U.S. patent application Ser. No. 14/949,906 (now issued as U.S. Pat. No. 9,876,968), and U.S. patent application Ser. No. 14/949,909 (now issued as U.S. Pat. No. 9,759,611), both filed on Nov. 24, 2015. All of the disclosures of the aforementioned applications are incorporated by reference in their entirety herein.

TECHNICAL FIELD

The present invention relates to the detection, imaging and measurement of infrared radiation.

BACKGROUND OF THE INVENTION

Industrial plants dealing with mining, production or storage of explosive or flammable gases and vapors such as hydrocarbons (methane, ethane, etc.), fuels of different kinds, hydrogen, acetylene, etc. are in constant danger of accidents. Explosions may cause fires, thus there is inherent danger from both the explosion itself and from the consequent ensuing fires. In addition, fires may result from a plethora of diverse causes, and when occurring in such plants, such fires may themselves cause explosions. The dangers are to both personnel and equipment, and the resulting damages may be in the worst cases loss of human lives and large financial losses to the owners of the plants.

Additionally, the release of the gases in question has a negative impact on the environment. As a result, regulatory laws have been introduced around the world to impose monitoring standards and heavy fines to companies that do not show due diligence in early detection of fires and prevention of inordinate releases of such materials.

The likelihood of explosions increases, up to a point, with increasing gas concentrations. Accordingly, over the past decades a large number of gas concentration measuring devices and fire detection instrumentation has been developed and used in mining, production and storage plants. Until recently only local detectors (for gases) or non-imaging IR and UV detectors (for flames) have been deployed. A gas detector of this type can easily miss the target gas if the gas cloud is present but does not physically meet the position of the detector (or path in case of cloud movement). This is due to the use of contact methods, such as chemical reactions with the gas. In the case of fire detection, the monitor is based on a single detector which does not provide an image of the field (i.e., scene) being monitored. Therefore, the monitor cannot provide the necessary information on the location and size of the fire.

Current industry instrumentation does not allow for the detection, identification, and location of the concentration, size and prognosis information of explosive gas or vapor clouds and flames due to incipient fires. Accordingly, current instrumentation cannot meet the additional requirements of being operable from a distance, in harsh environments, usually outdoors, and with minimal false alarms due to signals from other possible infrared sources, such as sun reflections, welding arcs, halogen lamps etc. The alarms provided by such detection instruments may be effectively used by the plant operators to prevent damages and losses of human lives through a number of possible actions. An example of such actions may be partial or total plant shut down, the request of fire department involvement, or other preventive or corrective action.

Furthermore, such infrared imaging devices can be used to quantitatively measure the radiance of each pixel of a scene only if the environment radiation changes (due mainly to environment temperature changes) contributing to the detector signals, can be monitored and corrected for. This is due to the fact that a quantitative measurement of infrared radiation from a scene is based on a mathematical relation between the detector signal and the radiation to be measured. This relation depends on the environment state during the measurement, and therefore the quantitative scene measurement can be done only if the environment state, and how the environment state affects that relation, is known during the measurement. The environment radiation sensed by the detector elements originates mainly from the optics and enclosures of the imaging device (besides the scene pixel to be monitored), and is a direct function of the environment temperature. If this radiation changes in time, it causes a drift in the signal, which changes its relation to the corresponding scene radiation to be measured and introduces inaccuracy.

This resulting inaccuracy prevents the use of such devices, especially in situations where they have to provide quantitative information on the gas to be monitored and have to be used unattended for monitoring purposes over extended periods of time, such as, for example, for the monitoring of a scene in industrial installations and facilities.

One known method for performing drift corrections is referred to as Non-Uniformity Correction (NUC). NUC corrects for detector electronic offset and partially corrects for detector case temperature drifts by the frequent use of an opening and closing shutter which is provided by the camera manufacturer. This NUC procedure is well known and widely employed in instruments based on microbolometer detectors. The shutter used for NUC is a moving part and therefore it is desirable to reduce the number of openings and closings of such a component when monitoring for gas leakages in large installations, requiring the instrument to be used twenty-four hours a day for several years without maintenance or recalibration. Frequent opening and closing of the shutter (which is usually done every few minutes or hours) requires high maintenance expenses.

To reduce the amount of shutter operations when using NUC techniques, methods for correcting for signal drift due to detector case temperature changes occurring between successive shutter openings have been developed by detector manufacturers, referred to as blind pixel methods. Known blind pixel methods rely on several elements of the detector array of the imaging device being exposed only to a blackbody radiation source placed in the detector case, and not to the scene radiation (i.e. being blind to the scene). However, such methods can only account and compensate for environmental temperature changes originating near and from the enclosure of the detector array itself, and not for changes originating near the optics or the enclosures of the imaging device. This is because in general there are gradients of temperature between the detector case and the rest of the optics and device enclosure. Therefore, known blind pixel methods may not satisfactorily compensate for environment radiation changes in imaging devices with large and/or complex optics, such as, for example, optics having an intermediate focal plane requiring at least two optical lenses, and optics having reflective and/or refractive surfaces for directing radiation in part through an optical lens towards the detector and/or in part directly towards the detector, as will be described below.

SUMMARY OF THE INVENTION

The present invention is directed to passive electro-optical instruments (i.e., devices), capable of detecting and imaging a cloud of hydrocarbon gas and/or a flame of burning material from a distance, distinguishing between the two types of materials, and for correcting for signal drift as a result of the changing environment.

The detection, imaging and measurement of hydrocarbon gas clouds and flames with the same device has a definite cost advantage over other methods using dedicated infrared imagers for each of the two types of events. This solution requires fewer instruments, fewer installations, and less maintenance, and therefore reduced costs. Infrared radiation imaging and measurement technology combined in a single device is a suitable candidate for such an endeavor, since both hydrocarbon gases and flames have spectral absorption and emission signatures in the appropriate range, as will be discussed in subsequent sections of this disclosure.

A key advantage of the devices of the present disclosure, among other advantages, is that they provide the capability of event diagnosis without human intervention, so in addition to the above application it can be used as a fixed installation for continuous monitoring and as a hand-held instrument for periodic plant maintenance and repair.

According to an embodiment of the teachings of the present invention there is provided, a device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising: (a) a detector of the radiation from the scene, the detector including a first and second plurality of detector elements and a filtering arrangement integrated thereon, the filtering arrangement including a first and second plurality of filtering elements, each of the first and second plurality of filtering elements having a respective pass band and stop band, the first wavelength region being within the pass bands of the first plurality of filtering elements and the stop bands of the second plurality of filtering elements and, the second wavelength region being within the pass bands of the second plurality of filtering elements and the stop bands of the first plurality of filtering elements; (b) an image forming optical component for forming an image of the scene on the detector, the radiation being imaged simultaneously, through an optical f-number of less than approximately 1.5, onto the first and second plurality of detector elements, the imaged radiation on the first plurality of detector elements including radiation in the first wavelength region and the imaged radiation on the second plurality of detector elements including radiation in the second wavelength region; and (c) electronic circuitry electronically coupled to the detector, the electronic circuitry configured to: (i) produce a pixel signal from each respective detector element, each of the pixel signals including information associated with the absorption or emission of radiation in one of the respective wavelength regions by each of the first and second materials, and (ii) determine the presence or absence of the first and second materials based on the produced pixel signals.

Optionally, the filtering arrangement is integrated by depositing a substrate on a surface of the detector, the substrate including the first and second plurality of filtering elements.

Optionally, the filtering arrangement is integrated by doping the first and second plurality of detector elements, such that the first plurality of detector elements is sensitive to radiation in the first wavelength region, and the second plurality of detector elements is sensitive to radiation in the second wavelength region.

Optionally, the first wavelength region includes radiation wavelengths between 3.15 and 3.5 microns, and the second wavelength region includes radiation wavelengths between 4.3 and 4.6 microns.

Optionally, the first and second plurality of filter elements are arranged such that each filter element of the first plurality of filter elements is adjacent to at least one respective filter element of the second plurality of filter elements.

Optionally, the detector includes separate first and second contiguous detector regions, the first detector region including the first plurality of detector elements, and the second detector region including the second plurality of detector elements.

Optionally, each filtering element of the first plurality of filtering elements is aligned with a respective detector element of the first plurality of detector elements and, each filtering element of the second plurality of filtering elements is aligned with a respective detector element of the second plurality of detector elements.

Optionally, the device further comprises: (d) a radiation directing arrangement for directing radiation from a field of view of the scene through the image forming optical component onto the detector, such that the radiation is separately imaged onto the first and second plurality of detector elements through the optical f-number of less than approximately 1.5.

Optionally, the radiation directing arrangement includes a reflective surface positioned substantially parallel to the optical axis of the device.

Optionally, the radiation directing arrangement includes first and second substantially wedge-shaped components.

Optionally, the detector includes a third plurality of detector elements, and the device further comprises: (d) a radiation source different from the scene, and the image forming optical component projects radiation from the radiation source onto the third plurality of detector elements, and wherein the electronic circuitry is further configured to: (iii) produce, for each detector element of the third plurality of detector elements, a second pixel signal from the radiation source projected by the image forming optical component onto the third plurality of detector elements, and (iv) modify each respective pixel signal, produced from the first and second plurality of detector elements, according to a predetermined function to produce a respective modified pixel signal, the predetermined function defining a relationship between a change in a respective second pixel signal and a change in the respective pixel signal, produced from the first and second plurality of detector elements, induced by a changing environment feature.

There is also provided according to an embodiment of the teachings of the present invention, a device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising: (a) a detector of the radiation from the scene, the detector including a plurality of detector elements, each detector element including a first and second detector element region, each of the first detector element regions being sensitive to radiation in the first wavelength region and each of the second detector element regions being sensitive to radiation in the second wavelength region; (b) an image forming optical component for forming an image of the scene on the detector, the radiation being imaged simultaneously, through an optical f-number of less than approximately 1.5, onto plurality of detector elements, such that the imaged radiation on each of the first detector element regions includes radiation in the first wavelength region and the imaged radiation on each of the second detector element regions includes radiation in the second wavelength region; and (c) an electronic circuitry arrangement electronically coupled to the detector, the electronic circuitry arrangement configured to: (i) produce a pixel signal from each respective detector element region, each of the pixel signals including information associated with the absorption or emission of radiation in one of the respective wavelength regions by each of the first and second materials, and (ii) determine the presence or absence of the first and second materials based on the produced pixel signals.

Optionally, the electronic circuitry arrangement includes a first and second electronic circuits, the first electronic circuit being electronically coupled to the first detector element regions, and the second electronic circuit being electronically coupled to the second detector element regions.

Optionally, the first electronic circuit is configured to produce a pixel signal from each respective first detector element region, and the second electronic circuit is configured to produce a pixel signal from each respective second detector element region.

Optionally, the first wavelength region includes radiation wavelengths between 3.15 and 3.5 microns, and the second wavelength region includes radiation wavelengths between 4.3 and 4.6 microns.

Optionally, the detector includes a second plurality of detector elements, and the device further comprises: (d) a radiation source different from the scene, and the image forming optical component projects radiation from the radiation source onto the second plurality of detector elements, and wherein the electronic circuitry arrangement is further configured to: (iii) produce, for each detector element of the second plurality of detector elements, a second pixel signal from the radiation source projected by the image forming optical component onto the second plurality of detector elements, and (iv) modify each respective pixel signal, produced from the first and second detector element regions, according to a predetermined function to produce a respective modified pixel signal, the predetermined function defining a relationship between a change in the respective second pixel signal and a change in the respective pixel signal, produced from the first and second detector element regions, induced by a changing environment feature.

There is also provided according to an embodiment of the teachings of the present invention, a device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising: (a) a detector of the radiation from the scene; (b) a static filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter; (c) an image forming optical component for forming an image of the scene on the detector, the radiation being imaged simultaneously, through an f-number of less than approximately 1.5, onto a first and second subset of pixels of the detector, the imaged radiation on the first subset of detector pixels including radiation in the first wavelength region and the imaged radiation on the second subset of detector pixels including radiation in the second wavelength region; and (d) electronic circuitry electronically coupled to the detector, the electronic circuitry configured to: (i) produce a pixel signal from each respective detector pixel, each of the pixel signals including information associated with the absorption or emission of radiation in one of the respective wavelength regions by each of the first and second materials, and (ii) determine the presence or absence of the first and second materials based on the produced pixel signals.

Optionally, the first wavelength region includes radiation wavelengths between 3.15 and 3.5 microns, and the second wavelength region includes radiation wavelengths between 4.3 and 4.6 microns.

Optionally, the detector includes a separate first and second detector region, the first detector region including the first subset of detector pixels, and the second detector region including the second subset of detector pixels, and the device further comprises: (e) a radiation directing arrangement for directing radiation from a field of view of the scene through the image forming optical component onto the detector, such that the radiation is separately imaged onto the first and second detector regions through the f-number of less than approximately 1.5.

Optionally, the radiation directing arrangement includes a reflective surface positioned substantially parallel to the optical axis of the device.

Optionally, the first filter is disposed proximate to the first detector region and the second filter is disposed proximate to the second detector region.

Optionally, the first filter is a first plate interposed between the first detector region and the image forming optical component, and the second filter is a second plate interposed between the second detector region and the image forming optical component.

Optionally, the first and second wavelength regions are in the mid wave infrared region of the electromagnetic spectrum, and the detector is sensitive to radiation in the first and second wavelength regions.

Optionally, the radiation directing arrangement includes first and second substantially wedge-shaped components.

Optionally, the first filter is disposed on one of a first surface or a second surface of the first wedge-shaped component, and the second filter is disposed on one of a first surface or a second surface of the second wedge-shaped component.

Optionally, the first surface of the first wedge-shaped component is a closest surface of the first wedge-shaped component to the image forming optical component, and the first surface of the second wedge-shaped component is a closest surface of the second wedge-shaped component to the image forming optical component, and the second surface of the first wedge-shaped component is a closest surface of the first wedge-shaped component to the scene, and the second surface of the second wedge-shaped component is a closest surface of the second wedge-shaped component to the scene.

Optionally, each of the first and second filters includes a plurality of filter elements, the plurality of filter elements being arranged such that each filter element of the plurality of filter elements of the first filter is adjacent to at least one respective filter element of the plurality of filter elements of the second filter.

Optionally, an indication of the presence or absence of the first and second materials is based on the difference between the pixel signals produced from the first and second subsets of pixels of the detector.

Optionally, the first material is a hydrocarbon gas cloud and the second material is a flame.

Optionally, the electronic circuitry is further configured to: (iii) if the hydrocarbon gas cloud is present, provide a measurement of the path concentration distribution of the hydrocarbon gas cloud based on at least a portion of the pixel signals.

There is also provided according to an embodiment of the teachings of the present invention, a device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising: (a) a detector of the radiation from the scene; (b) a filtering arrangement including a first and second filter, each of the filters having a respective pass band and a stop band, the first wavelength region being within the pass band of the first filter and the stop band of the second filter, and the second wavelength region being within the pass band of the second filter and the stop band of the first filter; (c) an image forming optical component for forming an image of the scene on the detector through an f-number of less than approximately 1.5; (d) a mechanism for positioning the filtering arrangement relative to the image forming optical component, such that, the radiation is alternately imaged through each of the first and second filters onto the same respective pixels of the detector; and (e) electronic circuitry electronically coupled to the detector, the electronic circuitry configured to: (i) produce, from each detector pixel, a respective pixel signal for each alternation of the radiation imaged through the first and second filters, the pixel signals including information associated with the absorption or emission of radiation in one of the respective wavelength regions by each of the first and second materials, and (ii) determine the presence or absence of the first and second materials based on the produced pixel signals.

Optionally, the first wavelength region includes radiation wavelengths between 3.15 and 3.5 microns, and the second wavelength region includes radiation wavelengths between 4.3 and 4.6 microns.

Optionally, each of the first and second filters includes a plurality of filter elements, the plurality of filter elements being arranged such that each filter element of the plurality of filter elements of the first filter is adjacent to at least one respective filter element of the plurality of filter elements of the second filter.

Optionally, the first material is a hydrocarbon gas cloud and the second material is a flame, and wherein the electronic circuitry is further configured to: (iii) if the hydrocarbon gas cloud is present, provide a measurement of the path concentration distribution of the hydrocarbon gas cloud based on at least a portion of the pixel signals.

Optionally, the first and second wavelength regions are in the mid wave infrared region of the electromagnetic spectrum, and the detector is sensitive to radiation in the first and second wavelength regions.

Optionally, the indication of the presence or absence of the first and second materials is based on, for each respective pixel of the scene, the averaging of a minority subset of pixel signals produced from the radiation imaged through the first filter, and the averaging of a minority subset of pixel signals produced from the radiation imaged through the second filter.

There is also provided according to an embodiment of the teachings of the present invention, a method for reducing drift induced by at least one changing environment feature when imaging radiation from a scene, the radiation including at least a separate first and second wavelength region, the method comprising: (a) focusing radiation from the scene through an image forming optical component onto a first region of a detector to produce at least a first pixel signal, the image forming optical component being positioned within a first enclosure volume; (b) positioning a radiation source proximate to the image forming optical component; (c) projecting radiation from the radiation source onto a second region of the detector to produce a second pixel signal, the first and second regions of the detector being non-overlapping regions and, the radiation from the radiation source being continuously projected onto the second region of the detector over the duration for which the radiation from the scene is focused onto the first region of the detector; and (d) modifying the first pixel signal based in part on a predetermined function to produce a modified pixel signal, the predetermined function defining a relationship between a change in the second pixel signal and a change in the first pixel signal induced by the at least one changing environment feature.

Optionally, the method further comprises: (e) determining the change in the first pixel signal induced by the changing environment feature based on the predetermined function, and wherein the modified pixel signal is produced by subtracting the determined change in the first pixel signal from the first pixel signal.

Optionally, the predetermined function is based on the correlation between the change in the second pixel signal and the change in the first pixel signal induced by the changing environment feature.

Optionally, the method further comprises: (e) determining the correlation, and the determining of the correlation is performed prior to performing (a).

Optionally, the radiation source is a blackbody radiation source, and the detector and the image forming optical component are positioned within a chamber having an adjustable chamber temperature, and a verification of the correlation is determined by: (i) forming a first set of signals provided by each pixel of the first detector region when imaging the blackbody radiation source at a constant temperature and at a range of different chamber temperatures; (ii) forming a second set of signals provided by the pixels of the second detector region at each of the different chamber temperatures; and (iii) verifying a correlation between the first and second sets of signals.

Optionally, the radiation source is a blackbody radiation source, and the detector and the image forming optical component are positioned within a chamber having an adjustable chamber temperature, and a determination of the correlation includes: (i) measuring a first reading of the first pixel signal at a first chamber temperature and measuring a subsequent reading of the first pixel signal at a subsequent chamber temperature; (ii) subtracting the first reading of the first pixel signal from the subsequent reading of the first pixel signal to define a first set; and (iii) measuring a first reading of the second pixel signal at the first chamber temperature, measuring a subsequent reading of the second pixel signal at the subsequent chamber temperature and subtracting the first reading from the second reading to define a second set.

Optionally, the modifying of the first pixel signal includes: (i) measuring a first reading of the first pixel signal at a first time instance and measuring a subsequent reading of the first pixel signal at a subsequent time instance; (ii) measuring a first reading of the second pixel signal at the first time instance and measuring a subsequent reading of the second pixel signal at the subsequent time instance; and (iii) subtracting the first reading of the blind pixel signal from the subsequent reading of the blind pixel signal to define a third set.

Optionally, wherein the modifying of the first pixel signal further includes: (iv) modifying the subsequent reading of the first pixel signal based on the third set in accordance with a correlation between the first and second sets.

Optionally, the determination of the correlation further includes: (iv) displaying the first set as a function of the second set.

Optionally, the determination of the correlation further includes: (iv) displaying the first set as a function of a third set, the third set being defined by the first chamber temperature and the subsequent chamber temperatures.

Optionally, the at least one environment feature includes environment temperature.

Optionally, the method further comprises: (e) filtering the radiation from the scene with a filter, such that, the imaged radiation on the first region of the detector includes radiation in one of the respective wavelength regions.

Optionally, the method further comprises: (f) positioning the filter at an intermediate focal plane between the image forming optical component and a second optical component for directing radiation from the scene towards the detector.

Optionally, the radiation source is positioned within the first enclosure volume.

Optionally, the radiation source is positioned at an intermediate focal plane between the image forming optical component and a second optical component for directing radiation from the scene towards the detector.

There is also provided according to an embodiment of the teachings of the present invention, a device for reducing drift induced by at least one changing environment feature when imaging radiation from a scene, the radiation including at least a separate first and second wavelength region, the device comprising: (a) a detector of the radiation from the scene and of radiation from the radiation source, the detector including a separate first and second detector region; (b) an optical system including an image forming optical component for continuously focusing the radiation from the scene and the radiation source onto the detector, the image forming optical component forming an image of the scene on the first detector region, through an optical f-number of less than approximately 1.5, and projecting radiation from the radiation source onto the second detector region, the optical system being positioned within a first enclosure volume; (c) a radiation source different from the scene, the radiation source being positioned proximate to the optical system; and (d) electronic circuitry electrically coupled to the detector configured to: (i) produce at least a first pixel signal from the imaged radiation on the first detector region; (ii) produce a second pixel signal from the radiation source projected by the image forming optical component onto the second detector region, and (iii) modify the first pixel signal according to a predetermined function to produce a modified pixel signal, the predetermined function defining a relationship between a change in the second pixel signal and a change in the first pixel signal induced by the at least one changing environment feature.

Optionally, the electronic circuitry is further configured to: (iv) determine the change in the first pixel signal induced by the at least one changing environment feature based on the predetermined function, and (v) subtract the determined change in the first pixel signal from the first pixel signal.

Optionally, the optical system further includes a second optical component and a mechanism for positioning the radiation source substantially at an intermediate focal plane, the intermediate focal plane being between the second optical component and the image forming optical component.

Optionally, the device further comprises: (e) a filter for filtering the radiation from the scene, such that, the imaged radiation on the first region of the detector includes radiation in one of the respective wavelength regions.

Optionally, the optical system further includes a second optical component and a mechanism for positioning the filter substantially at an intermediate focal plane, the intermediate focal plane being between the second optical component and the image forming optical component.

BRIEF DESCRIPTION OF THE DRAWINGS

The invention is herein described, by way of example only, with reference to the accompanying drawings, wherein:

FIG. 1 is a plot of the spectral absorptance of methane gas;

FIG. 2 is a plot of the spectral absorptance of ethane gas;

FIG. 3 is a plot of the spectral absorptance of propane gas;

FIG. 5 is a plot of the infrared emission spectra of cardboard and wood;

FIG. 6 is a plot of the frequency content of a fuel flame;

FIG. 7 is a plot of the self-emission spectrum of a hydrogen flame;

FIG. 10 is a schematic representation of a checkerboard pattern filtering arrangement for performing detection and imaging of the radiation from the scene using the configurations of the device of FIGS. 9A and 9B;

FIG. 11 is a schematic representation of an alternate configuration of the checkerboard pattern filtering arrangement of FIG. 10, according to an embodiment of the invention;

FIGS. 12 and 13 show schematic representations of groups of detector pixels corresponding to a single scene pixel, according to an embodiment of the invention;

FIG. 14 is a schematic side view illustrating a device with a wedge configuration for detecting and imaging radiation from a scene in two separate wavelength regions without moving parts, according to an embodiment of the invention;

FIG. 16 is a schematic front view illustrating a detector and the resulting image formed on the detector, according to an embodiment of the invention;

FIGS. 18A and 18B are schematic side views illustrating filtering alternatives of the device of FIG. 14, according to embodiments of the invention;

FIGS. 19A and 19B are schematic side views illustrating filtering alternatives of the devices of FIGS. 14 and 17, according to embodiments of the invention;

FIG. 21A is an isometric exploded view illustrating a detector array with a filter substrate in a checkerboard pattern, according to an embodiment of the invention;

FIG. 21B is a top view corresponding to FIG. 21A;

FIGS. 21C and 21E are isometric exploded views illustrating a detector array with alternate pattern configurations of the filter substrate of FIGS. 21A and 21B;

FIGS. 21D and 21F are side views corresponding to FIGS. 21C and 21E, respectively;

FIGS. 22A-22C are schematic front views illustrating configurations of a detector having a first set of detector elements sensitive to a first wavelength region and a second set of detector elements sensitive to a second wavelength region, according to an embodiment of the invention;

FIG. 23 is a schematic front view illustrating a detector having an array of detector elements in which each detector element includes a first sub-element sensitive to a first wavelength region and a second sub-element sensitive to a second wavelength region, according to an embodiment of the invention;

FIG. 25 is a schematic side view illustrating a device for drift correction according to an embodiment of the invention;

FIG. 26 is a schematic front view illustrating a detector array of the device of FIG. 25;

FIG. 28A is a schematic front view illustrating a detector array of the device of FIG. 27;

FIG. 28B is a schematic front view illustrating blind pixels and imaged pixels according to an embodiment of the invention;

DESCRIPTION OF THE PREFERRED EMBODIMENTS

Figure 4:
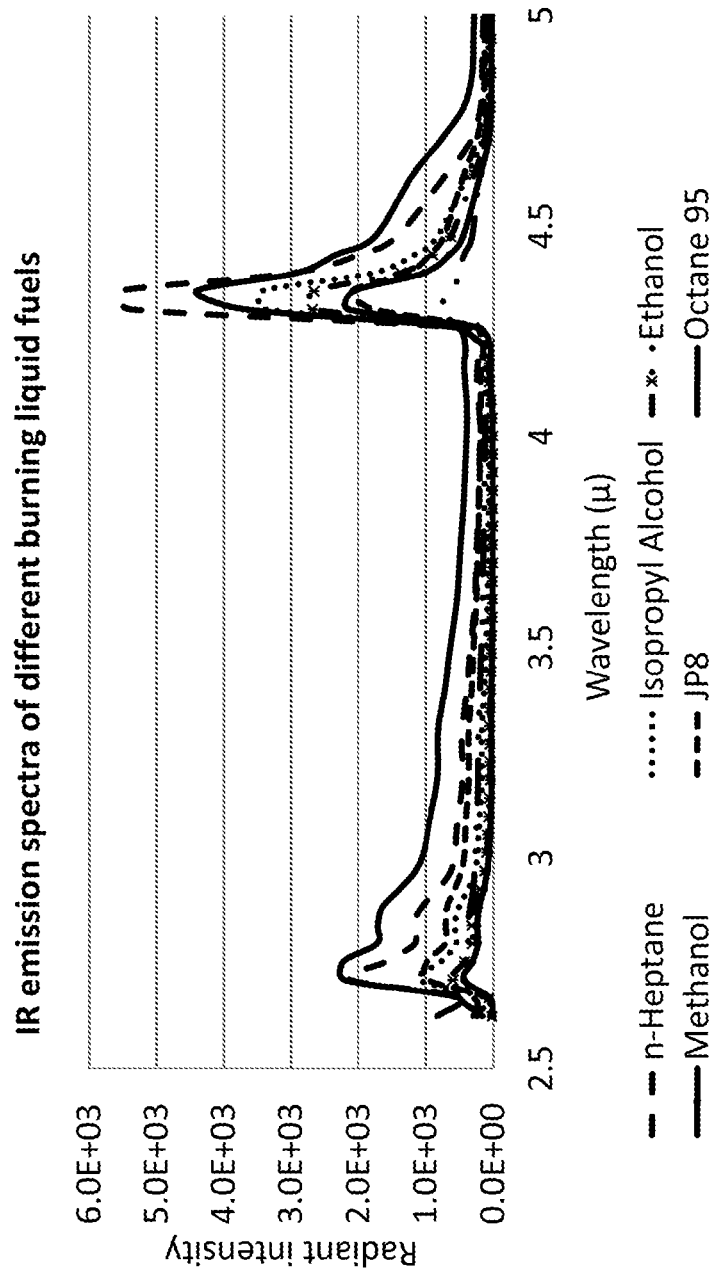
FIG. 4 is a plot of the infrared emission spectra of flames of various burning gas and liquid fuels.

The principles and operation of the device according to the present invention may be better understood with reference to the drawings and the accompanying description.

Before explaining at least one embodiment of the invention in detail, it is to be understood that the invention is not necessarily limited in its application to the details of construction and the arrangement of the components and/or methods set forth in the following description and/or illustrated in the drawings and/or the examples. The invention is capable of other embodiments or of being practiced or carried out in various ways.

The present invention is a device for detecting and imaging both a cloud of hydrocarbon gas and/or a flame of burning material. The device performs the detection and imaging from a distance and can distinguish between the two types of events (i.e. hydrocarbon gas and flame of burning material). The device also corrects for signal drift resulting from the changing environment around the device.

As examples, FIGS. 1-3 show the absorptance of 1 (ppm)×(meter) of methane (in units of $Log_{10}$ of inverse transmittance T), ethane and propane in the 2800 to 3200 wavenumbers ($cm^{-1}$) range (equivalent to 3.125 to 3.57 micron range).

Note that ethane and propane above and the other longer chain hydrocarbons butane, pentane and hexane, have absorptance between 3.3 and 3.5 microns while methane absorbs in a wider range, from 3.15 to 3.5 microns. Also note that none of such gases absorb infrared radiation in the 4.3 to 4.6 micron range, where flames emit large amount of radiation.

Typical emission spectra of flames due to various liquid fuels such as n-heptane, lead free, jet, diesel and others are shown in FIG. 4. The feature around 2.7 microns is due to self-emission of hot water molecules in the flame, whereas the 4.3 to 4.7 micron feature is due to the hot $CO_2$ gas in the flame.

Similar infrared spectra of cardboard and wood are shown in FIG. 5. The strong features due to water (near 2.7 microns, due to water and 4.5 microns, due to carbon dioxide) are similar to the flames of liquid fuels of FIG. 4.

Such flames also flicker with characteristic frequencies. Radiometric measurements of n-heptane flame and other fuel flames as a function of time in both the 3 to 5 micron range and 8 to 14 micron range show that 90% of the total emitted energy varies with frequency components up to 5.5 Hz. With a fast enough camera gathering this information, the probability of detection of a liquid fuel flame may be increased. FIG. 6 shows the frequency content of n-Heptane flames as an example.

Note that in the 3 to 5 micron range the hydrogen flame emission is very small compared to the fuel flames emission. It is especially much smaller in the 4.3 to 4.6 micron range, where the flames due to liquid fuels show an especially large emission.

The absorptance data of the hydrocarbon gases are available to the public, for example, from Pacific Northwest National Laboratory in Richland Wash., USA, and are high resolution data. The flame emission spectra and time/frequency behavior have been measured by an SR 5000 N spectroradiometer of CI Systems, an instrument capable of measuring self-emission spectra of objects, calibrated in units of spectral radiance (Watts/((steradian)×(cm$^2$)×(μ)) or spectral radiant intensity in Watts/((steradian)×(μ)).

For the purpose of the present disclosure, it is useful to summarize the spectral data presented in FIGS. 1-7, as will described below.

Hydrocarbon gas absorption spectrum has a significant feature between 3.15 and 3.5 microns in methane and between 3.3 and 3.5 microns in the others. None of these gases have absorption in the 4.3 to 4.6 micron range, where burning flames (except hydrogen) have a strong self-emission feature. The flames, represented by n-heptane in FIG. 6 as an example, show a time behavior of the infrared emission containing frequency components up to 5.5 Hz.

The device of the present disclosure is applicable for use in industrial locations, and is of particular value for both in-door and out-door use, and to provide an alarm in a plant when an explosive gas may be found in above than dangerous amounts, or when a fire has broken out in a space within the field of view of the device. The device is preferably based on an imaging camera (i.e., detector comprised of an array of detector elements) sensitive in the 1 to 4.5 micron spectral range, where both hydrocarbon gases and flames have strong spectral absorption or emission features. The 1 to 4.5 micron spectral range includes portions of the Near Infrared (NIR), Short-Wave Infrared (SWIR), and Mid-Wave Infrared (MWIR) regions of the electromagnetic spectrum. As will be further discussed, the detector array may also be sensitive to radiation in the Long-Wave Infrared (LWIR) region of the electromagnetic spectrum. Elements of the device include the optics to collect this IR radiation from the scene, a number of alternative spectral IR radiation filtering methods, and suitable algorithms especially designed to extract the information needed for detection, real-time imaging and event identification from the resulting pixel signals.

1. General Elements of the Device of the Present Disclosure:

The central element is a camera (i.e., detector array) sensitive to infrared radiation in the spectral range preferably between 3 and 4.6 microns is built with collection optics to receive such radiation from a scene and re-image the radiation on the camera through two band pass filters, one covering the range 3.15 and 3.5 microns and one covering the range 4.3 to 4.6 microns. It is well known in the art that a gas cloud interposed between a background and such a camera may be detected and imaged, and its path concentration measured (in units of (ppm$_{volume}$)×(meter)), provided the background temperature is different than the cloud temperature, and the signals produced from the detector array are compared through a so-called in-band filter (transmitting radiation in the absorption wavelength range of the gas, in our case 3.15 to 3.5 microns) and the so-called out-of-band filter (transmitting radiation outside the absorption wavelength range of the gas): in this case the difference between the two signals is positive or negative depending on whether the temperature difference between background and cloud is negative or positive respectively. Analogously, from what is shown in FIG. 4 above, the filter transmitting 4.3 to 4.6 micron radiation is in-band with respect to flames of burning fuels, methane, and solid materials, while the 3.15 to 3.5 filter is out-of-band with respect to the same flames (the signal will be higher in the former and smaller in the latter spectral range). In this way, if the camera pixels are exposed to both filters, either successively or simultaneously by using a split-image method described below, the detection and identification of hydrocarbon gases and flames can be achieved. The appropriate signal differences through the two filters for each pixel will provide an indication as to whether the device is exposed to a flame (large and positive) or to a hydrocarbon gas (much smaller and positive or negative according to the background-object temperature difference).

The following features are important in this invention for becoming used in practice, even though in principle are only optional.

The detector array used in the camera is preferably a PbSe (lead selenide) uncooled or thermoelectrically cooled instead of other more expensive cryogenically cooled detectors, such as InSb (indium antimonide) arrays, which are sensitive in the same spectral range. PbSe detectors are becoming available commercially today. For example, St. Johns Optical Systems in Sanford and Lake Mary, Fla., US, offers such detectors, developed by Northrop Grumman, also in the US. New Infrared Technologies (NIT), a company in Madrid, Spain offers a number of PbSe array detector models.

Alternatively, the detector array used in the camera may be a Quantum Well Infrared Photodetector (QWIP) type array. The use of such QWIP type arrays requires that the detector array be manufactured such that the resulting wavelength sensitivity is in the appropriate spectral range, as will be described in more detail below.

Time or frequency analysis of the signals, in addition to the in-band-out-of-band comparison may be used in the mathematical algorithms of the device for better distinction between a gas cloud and a flame event, and between a flame and other infrared sources, yielding lower false alarm rate. In fact, flames flicker at characteristic frequencies that may aid in their identification.

Such PbSe detector arrays are sensitive to radiation in the MWIR region of the electromagnetic spectrum. Alternatively, microbolometer type arrays may be used for sensitivity to radiation in the LWIR region of the electromagnetic spectrum.

2a. Gas Measurement:

In the following section, it is shown how the (ppm$_{volume}$)× (meter) of the gas can be measured in a pixel successively exposed to the in-band and out-of-band wavelength range by measuring the radiance difference in these two ranges.

It has been well known for many years that it is possible to detect the presence of a gas in the air by measuring the infrared self-emission of the background of the gas cloud in two different wavelengths, one which is absorbed by the gas and one which is not, provided that the background and gas are not at the same temperature. The radiance difference R reaching the measuring instrument between the two wavelengths $w_0$ (not absorbed) and $w_G$ (absorbed by the gas), can be expressed in terms of the background radiance B, the gas temperature $T_G$ (usually equal to the air temperature, and we assume that it is known by measurement) and the gas transmittance to at the absorbed wavelength as follows:

$$R = B - B^* t_G - (1-t_G)^* Pl(T_G, w_G) = (1-t_G)^* \{B - Pl(T_G, w_G)\} \quad (1)$$

where $Pl(T_G, w_G)$ is the Planck function at temperature $T_G$ and wavelength $w_G$. Two simplifications are used in equation (1) which are not important for the sake of this explanation because the associated phenomena can both be calibrated out in the more general case: i) atmospheric transmittance is assumed to be 1, and ii) background radiance in and out of the gas absorption band are equal.

It is obvious from equation (1) that in the case that B is equal to $Pl(T_G, w_G)$, the radiance difference R is equal to zero, irrespective of the value of $t_G$, and in this case no information can be inferred on the quantity to. However, if B is different than $Pl(T_G, w_G)$, then equation (1) can be solved for $t_G$ as follows:

$$t_G = 1 - \frac{R}{B - Pl(T_G, w_G)} \quad (2)$$

All parameters on the right hand side of equation (2) are known: B is known because it is measured in the non-absorbing wavelength $w_0$, or in the wavelength $w_G$ in the absence of gas, Pl is known because $T_G$ is measured and $w_G$ is known, and R is measured. Therefore, $t_G$ is known from equation (2). If the molecular absorptance, $A_G$, of the specific gas being monitored is known from the literature at $w_G$, then $t_G$ gives a measure of the product of average gas volume concentration in the cloud, multiplied by the thickness of the cloud itself, or the so called concentration times length (or path concentration) value of the cloud. In fact, by the Lambert-Beer law as follows:

$$t_G = e^{-nA_G l} \quad (3)$$

where l is the path length or thickness of the cloud and n is the average volume concentration of the gas being measured in the cloud, both corresponding to a specific pixel being examined. Equation (3) can then be inverted to yield the value of the product nl for the particular pixel in question:

$$nl = \frac{1}{A_G} \ln\left(\frac{1}{t_G}\right) \quad (4)$$

If $t_G$ in (2) is measured to be less than 1, then nl in (4) is finite and there is gas in the region of the pixel in question, in the amount nl ($ppm_{volume}$)×(meter). If to from (2) is equal to 1, then nl=0 in (4), and there is no gas. Note that $t_G$ values less than 0 or larger than 1 are not physical, since $t_G$ is a transmittance and is therefore bounded between 0 and 1.

2b. Flame Measurement:

In the case that a flame is present in a pixel of the scene instead of a gas cloud, the detector pixel signal $S_{flame}$ is nearly zero when exposed to filter $w_G$ and high when exposed to filter $w_0$. This is due to the definition of the band pass of the two filters 4a and 4b and to the shape of the flame emission spectra as shown in FIG. 4. The difference of the signals measured through the two filters 4a and 4b, or simply the $w_0$ signal (from the filter 4b), indicates the presence or absence of the flame in the corresponding scene pixel.

In the following sections, the various embodiments of a device will be presented with different optical and filtering configurations for achieving the gas concentration measurement and flame detection functionality previously discussed. It is noted that the optical components and filtering components of these embodiments are typically retained within an optical casing, filter casing or the like, which can be considered to be an enclosure volume, for maintaining the position and orientation of the optical and filtering components.

Figure 8:
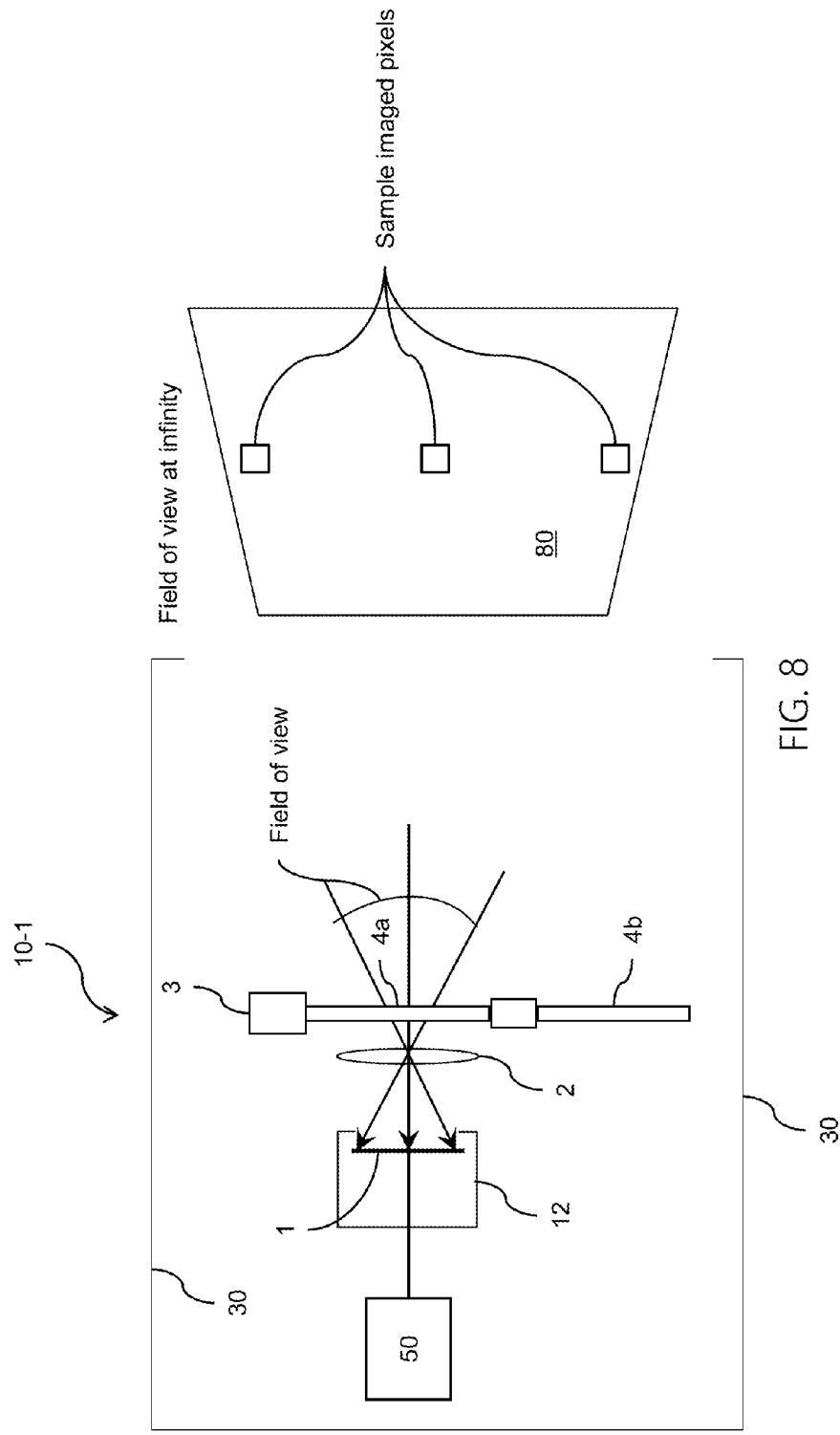
FIG. 8 is a schematic side view illustrating a device for detecting and imaging radiation from a scene in two separate wavelength regions, according to an embodiment of the invention.

3a. Successive Exposure to In-Band and Out-of-Band Filtering:

FIG. 8 depicts an embodiment of a device 10-1 for detecting and imaging a cloud of hydrocarbon gas and a flame (i.e, a scene 80). The device 10-1 includes an objective lens 2 (i.e., collection optics), positioned in front of a detector array 1 and a two-position filter holder or wheel 3 containing two filters (a first filter 4a and a second filter 4b), either in front of the objective lens 2 or between the objective lens 2 and the detector array 1. The first filter 4a, centered at $w_G$, is the in-band gas filter with a pass band between 3.15 and 3.5 microns or between 3.3 and 3.5 microns, or an optimized range between 3.15 and 3.5 microns. The second filter 4b, centered at $w_0$, is the out-of-band gas filter with a pass band between 4.3 and 4.6 microns. The first filter 4a (i.e., the filter centered at $w_G$) serves also as the out-of-band flame filter, while the second filter 4b (i.e., the filter centered at $w_0$) serves also as the in-band flame filter. The filter holder or wheel alternates the two filters in the optical train, successively exposing the detector to the two different spectral ranges. Only the principal rays of the central, top and bottom pixels of the field of view (FOV) are shown. The filters 4a and 4b can be alternately placed between the lens 2 and the detector array 1 or between lenses in a multiple lens system design.

Note that the configuration of the device 10-1 as shown in FIG. 8 can be preferably designed with a large numerical aperture of the objective lens 2 to exploit the best possible detector sensitivity (or low f-number, which is in general kept as close to 1 as possible, especially when using uncooled infrared detector arrays). Accordingly, it is preferred that the objective lens 2 of the device 10-1 has an f-number less than 1.5, and as close to 1 as possible (i.e., f/1.5 or less). A different configuration, using a dichroic beamsplitter to split the incoming beam into two beams to be filtered separately in the two wavelengths and two separate detectors can be used, but would be more expensive because of the additional detector cost. A further similar configuration using, besides the dichroic filter, an additional beam combiner and chopper may be used to limit the design to the single array detector, but in this case the chopper, needed to switch between the two wavelengths in synchronization with the detector frame capture rate, is a low reliability moving part. These last two configurations require more complicated optics to avoid decreasing the numerical aperture of the focusing optics at the detector and degrade the device sensitivity.

Note that a whole frame image of the scene 80 is exposed to only one of the two band pass filters 4a and 4b in succession. The information needed for gas or flame detection and imaging is achieved by the acquisition of at least two frames while the two filters 4a and 4b are successively positioned in the optical train by the rotation or translation of the holder or wheel 3, in such synchronization that each frame is acquired through one of the filters (4a or 4b). The sequence of exposure to the two filters 4a and 4b can be repeated as many times as desired, whether for averaging to achieve higher signal to noise ratio or for any other reason. The sequence may be composed also by several frames through one of the filters and then several frames through the other filter, instead of alternating frames.

Image acquisition electronics 50 are electrically coupled to the detector array 1 for processing output from the detector array 1 in order to generate and record signals corresponding to the detector elements (i.e., pixels) for imaging the scene 80. The image acquisition electronics 50 includes electronic circuitry that produces corresponding pixel signals for each pixel associated with a detector element. As a result of the radiation being imaged on a multiple of detector elements, the image acquisition electronics 50 produces multiple corresponding pixel signals.

Figure 20:
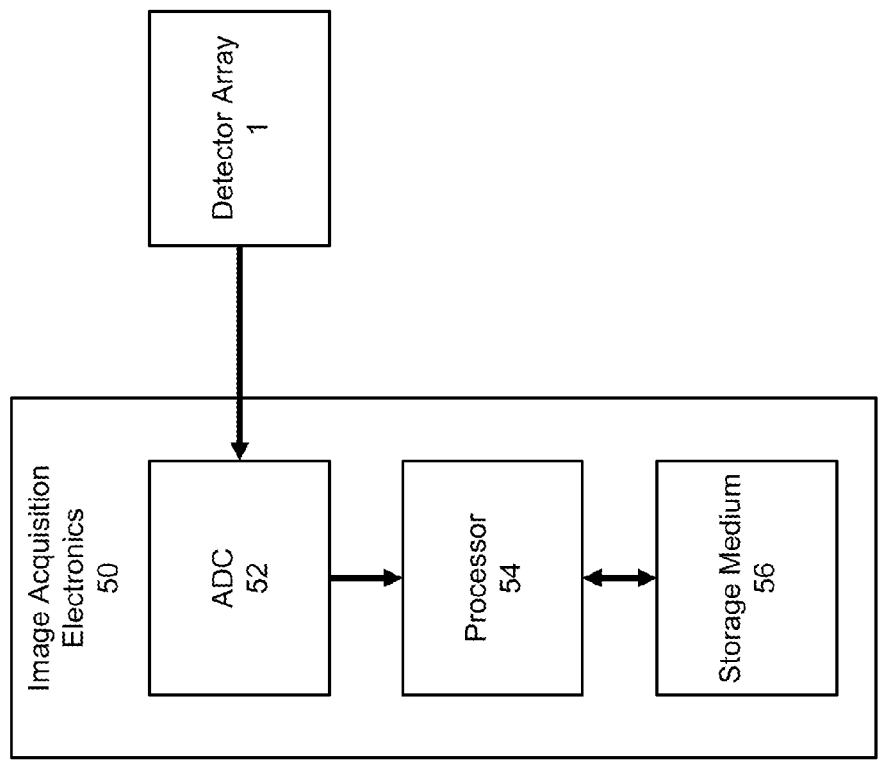
FIG. 20 is a block diagram of image acquisition electronics coupled to a detector array, according to an embodiment of the invention.

As shown in FIG. 20, the image acquisition electronics 50 preferably includes an analog to digital conversion module (ADC) 52 electrically coupled to a processor 54. The processor 54 is coupled to a storage medium 56, such as a memory or the like. The ADC 52 converts analog voltage signals from the detector elements into digital signals. The processor 54 is configured to perform computations and algorithms for determining and/or indicating the presence or absence of the gas cloud path concentration distribution and/or flame, as well as imaging and measuring the gas cloud path concentration distribution and/or flame, as described in Sections 2a and 2b, based on the digital signals received from the ADC 52.

The processor 54 can be any number of computer processors including, but not limited to, a microprocessor, an ASIC, a DSP, a state machine, and a microcontroller. Such processors include, or may be in communication with computer readable media, which stores program code or instruction sets that, when executed by the processor, cause the processor to perform actions. Types of computer readable media include, but are not limited to, electronic, optical, magnetic, or other storage or transmission devices capable of providing a processor with computer readable instructions.

The above mentioned components of the device 10-1 are positioned within a casing defined by internal walls 30 of the device 10-1. Furthermore, the detector array 1 is preferably maintained within a detector case 12, which in turn is positioned within the casing of the device 10-1. Therefore, the internal walls 30 can be considered to be an enclosure volume for maintaining the position and orientation of the optical components and the detector array 1.

Figure 9B:
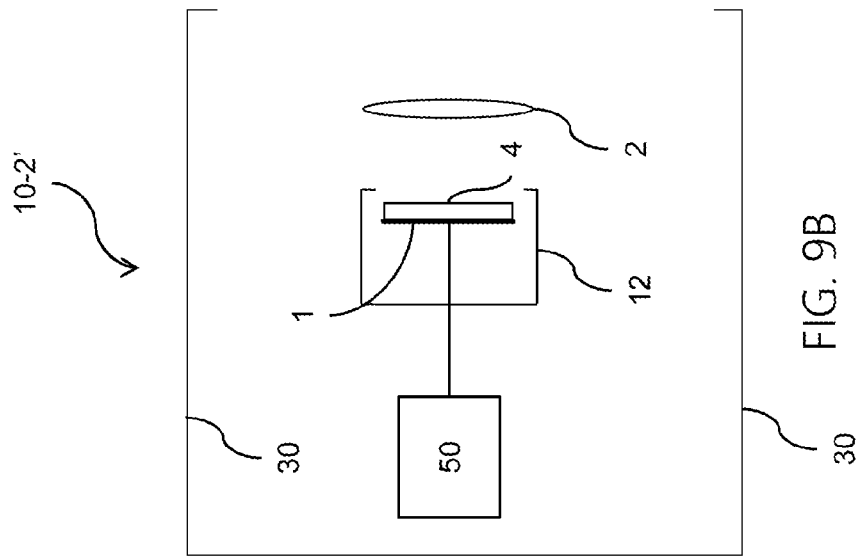
FIG. 9B is a schematic side view illustrating an alternate configuration of the device of FIG. 9A in which the detecting and imaging of radiation from the scene is accomplished with no moving parts.
Figure 9A:
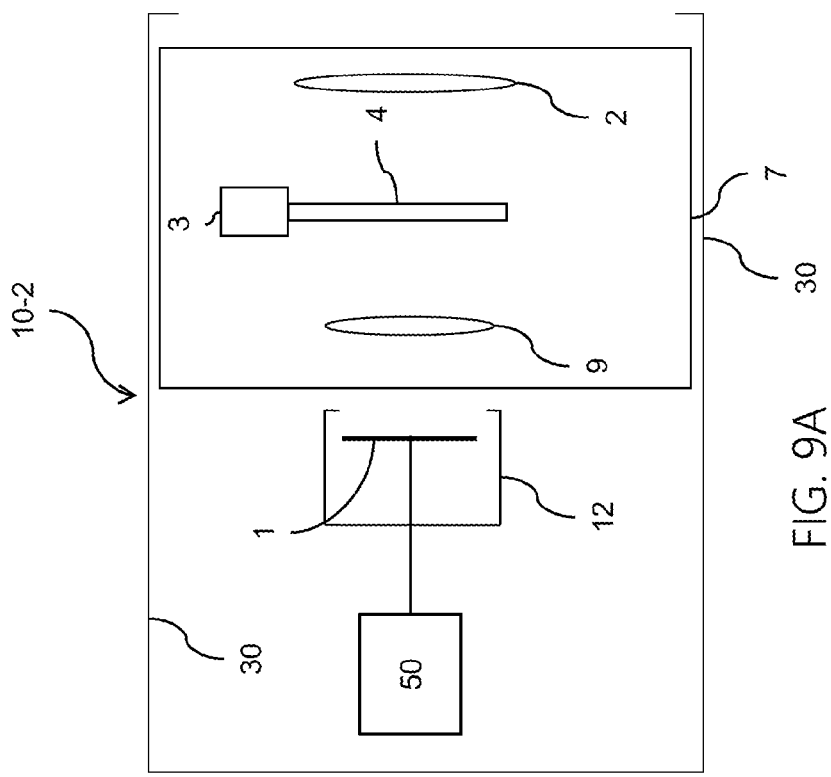
FIG. 9A is a schematic side view illustrating a device for detecting and imaging radiation from a scene in two separate wavelength regions using a checkerboard pattern filtering arrangement, according to an embodiment of the invention.

3b. Exposure to In-Band and Out-of-Band Filtering by Pattern Filtering:

FIGS. 9A and 9B depict different configurations of a device 10-2 and 10-2' which are alternative embodiments of the device 10-1, which uses an alternate method of switching the exposure of the pixels of the detector to the two band pass filters centered at wavelengths $w_G$ and $w_0$ by "patterned filtering". This method may be implemented both statically (with some degree of loss of spatial resolution as explained below) or dynamically by movement of an optical filtering device. In the latter case the extent of movement is much smaller in amplitude than in the method of Section 3a, and can be performed with a simpler and cheaper motor, like a piezoelectric oscillator, instead of a rotary or translatory motor like in the previous section.

Referring to FIG. 10, a checkerboard patterned filter 4 is implemented as the optical filtering device. The filter 4 can be used as a replacement for the two filters 4a and 4b of FIG. 8, and may be placed in an intermediate focal plane (FIG. 9A), an image plane of the scene, which is then re-imaged on the detector array, or on or as close as possible to the detector plane itself (FIG. 9B). For the device 10-2, the positioning of the checkerboard patterned filter 4 in an intermediate focal plane is depicted schematically in FIG. 9A. The lens system of the device 10-2 includes the objective lens 2 and a re-imaging optical lens 9 (i.e., re-imaging optics), which together constitute collection optics 7. For the device 10-2', the positioning of the checkerboard patterned filter 4 on the detector plane is depicted schematically in FIG. 9B. The size of the squares on the board is optically matched to the size of the detector pixel, and each square is coated so that a particular square corresponds to one or the other of the filters 4a and 4b.

In FIG. 10, the white squares (4a-1, 4a-2, ... , 4a-N) correspond to the first filter 4a (i.e., the filter centered at $w_G$). Each white square (4a-1, 4a-2, ... , 4a-N) represents an individual element of the first filter 4a (i.e., the filter centered at $w_G$). Similarly, the diagonally hatched squares (4b-1, 4b-2, ... , 4b-N) correspond to the second filter 4b (i.e., the filter centered at $w_0$). Each diagonally hatched square represents an individual element of the second filter 4b (i.e., the filter centered at $w_0$). The elements of the first and second filters 4a and 4b occupy the entire detector plane. The filter 4 is oscillated the length (i.e., amplitude) of a square along the horizontal or vertical direction relative to the detector plane. This successively exposes each detector pixel to one or the other of the band pass filters. The oscillation is performed in synchronization with the detector frame acquisition (i.e., the image acquisition electronics 50) in order to provide the necessary scene information for performing the gas measurement and flame detection described in Sections 2a and 2b above, as carried out by the processor 56 of the image acquisition electronics 50.

The filter combination shown in FIG. 10 can be alternatively implemented with alternating rows or columns of the elements centered at $w_G$ and $w_0$ instead of a checkerboard, as in FIG. 11. In the implementation of the filter 4 depicted in FIG. 11, the movement of the filter 4 is in the vertical direction relative to the detector plane. The movement amplitude is equal to the length of one square, as previously described.

Note that many other similar configurations may be conceived, as for example the alternating stripes of FIG. 11 arranged in columns instead of rows. In this case the movement is in the horizontal direction relative to the detector plane.

In the non-limiting example configurations illustrated in FIGS. 10 and 11, a total of 2N filter elements are depicted, with each of the first and second filters having N filter elements.

A checkerboard or stripe configuration as in FIGS. 10 and 11 may be also static, either on an intermediate focal plane as mentioned above, or positioned very close to the detector plane, so that each square or row is exactly spatially registered with each pixel or row of pixels, respectively. As mentioned, such a configuration of the device 10-2' is depicted schematically in FIG. 9B. In this case the spatial resolution or field of view is decreased because one scene pixel is now made of at least two or four (or more) detector pixels. In order to obtain the information on the gas or flame presence, the signals of detector pixels corresponding to either of the band pass filters is summed together and averaged. The summing and averaging of the signals may be executed by the processor 54. Accordingly, the entire scene 80 is imaged onto the detector 1. The neighboring detector pixels produce signals, via the image acquisition electronics 50, which correspond to the same portion of the scene 80 as filtered through each of the filters 4a and 4b.

In FIG. 12, a group of four detector pixels is shown which correspond to a single scene pixel. The signals of the pixels filtered through the white squares (i.e., 4a-1 and 4a-2 corresponding to the filter centered at $w_G$) are averaged to obtain the in-band signal of the scene pixel. Similarly, the signals of the pixels filtered through the diagonally hatched squares (i.e., 4b-1 and 4b-2 corresponding to the filter centered at $w_0$) are averaged to obtain the out-of-band signal of the scene pixel. In such a configuration, the number of scene pixels is reduced by a factor of two in both the vertical and horizontal directions relative to the detector plane.

In FIG. 13, a group of two detector pixels is shown which correspond to a single scene pixel. In such a configuration, no averaging is necessary, and the number of scene pixels is reduced by a factor of two only in the vertical direction relative to the detector plane.

As should be understood, both checkerboard patterned filter implementations as depicted in FIGS. 10 and 11 can be used with each of the devices 10-2 and 10-2', depicted in FIGS. 9A and 9B, respectively. Furthermore, the objective lens 2 of the devices 10-2 and 10-2' can be designed with a large numerical aperture (i.e., f/1.5 or less and as close as possible to f/1) similar to the objective lens of the device 10-1.

Similar to the device 10-1, the components of the devices 10-2 and 10-2' are positioned within a casing defined by internal walls 30 of the respective devices 10-2 and 10-2'. Also similar to the device 10-1, the detector array 1 of each of the respective devices 10-2 and 10-2' are preferably maintained within a detector case 12.

3c. Exposure to In-Band and Out-of-Band Filtering by Split Image Wedge Configuration:

FIG. 14 shows an embodiment of a device 10-3 that uses an optical configuration referred to as a "split image wedge" configuration. The object (scene 80 against the background 90) on the right side is imaged on the detector plane through the two wedge-shaped components (5 and 6) and the objective lens 2, so that two images of the scene 80 and the background 90 are formed on two halves of the surface of the detector array 1 (a first half 1a and a second half 1b), as shown in FIG. 16. The scene 80 and the background 90 are imaged simultaneously on two halves of the detector plane, forming two identical images. The two images are formed through the two band pass filters centered at $w_G$ and $w_O$, respectively, implemented as coatings 4a and 4b, respectively, so that each scene pixel is measured through an in-band and an out-of-band filter by two different detector pixels at the same time.

The wedge shaped components 5 and 6 together with the objective lens 2 constitute collection optics 7. Most preferably, the detector array 1 of the device 10-3 is a PbSe type array sensitive to radiation in the MWIR region of the electromagnetic spectrum.

The device 10-3 has the advantage that no filter movement is required and that the in-band and out-of-band signals are acquired at the same time. This may improve on potential drifts between the two signals due to gas cloud movement. The disadvantage is that the detector area is exploited for one half of the field of view that could be obtained with the same objective optics and without the wedges. Similar to the device 10-1 of FIG. 8 and the devices 10-2 and 10-2' of FIGS. 9A and 9B, respectively, the device 10-3 includes image acquisition electronics 50 for generating digital signals and for performing computations and algorithms for determining and/or indicating the presence or absence of the gas cloud path concentration distribution and/or flame, as well as imaging and measuring the gas cloud path concentration distribution and/or flame.

The same infrared radiation from the scene 80 is imaged onto each of the two detector regions 1a and 1b, with each region of the detector imaging the scene 80 in a different wavelength range.

Figure 15:
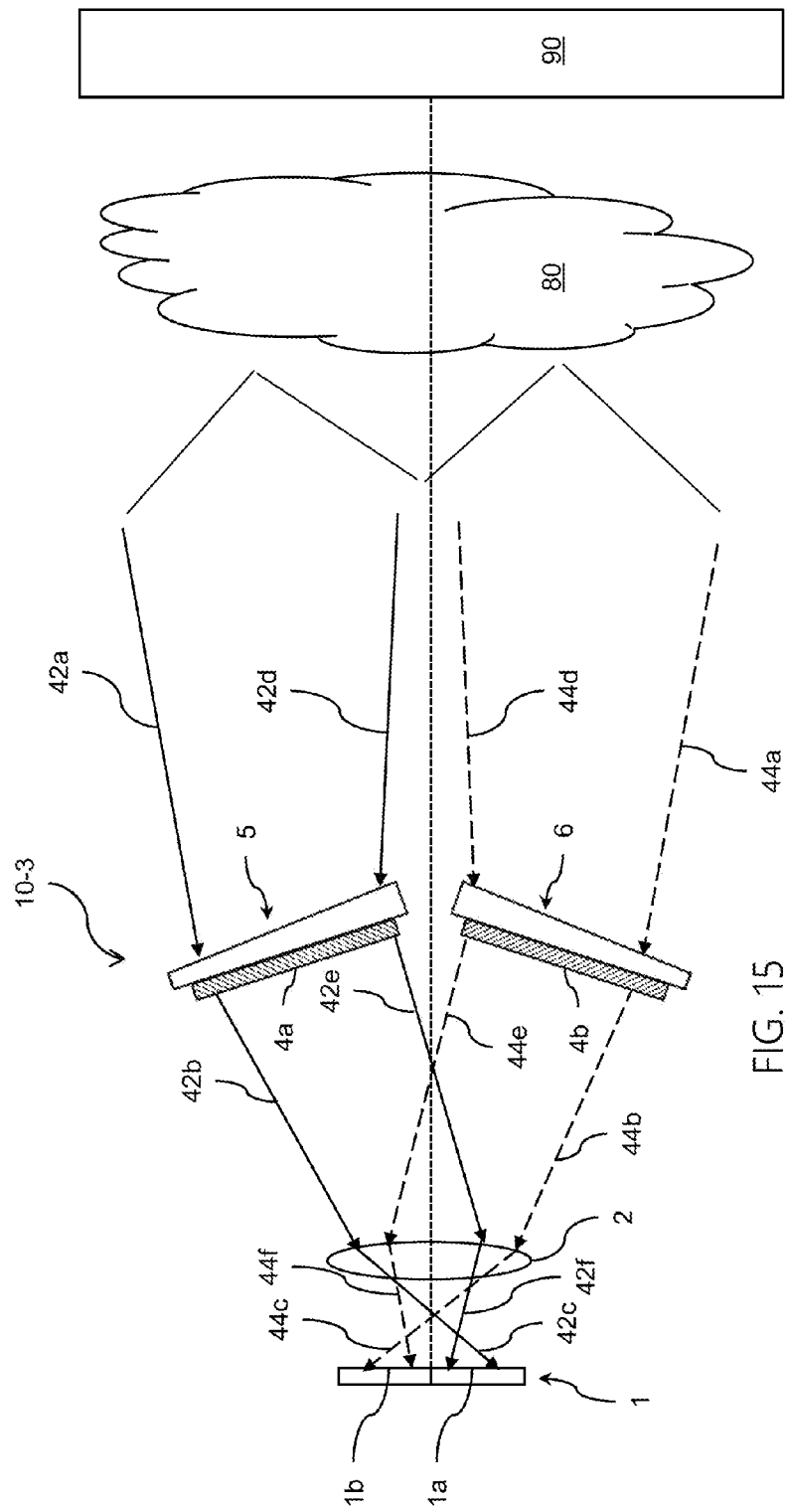
FIG. 15 is a schematic side view illustrating the traversal of incident rays from the scene and the scene background through the device of FIG. 14.

FIG. 15 depicts the traversal of incident rays 42a-42f and 44a-44f from the scene 80 to the detector array 1. The broken lines between the scene 80 and the device signifies that the distance between the scene 80 and the device as depicted in FIG. 15 is not to scale. In general, the distance between the scene 80 and the device is much larger than the size of the device itself, and is typically on the order of tens or hundreds of meters. Additionally, the broken line signifies that the two bundles of rays 42a, 42d and 44a, 44d both originate from the entire scene and not from one half of the scene.

Note that although only four incident rays 42a, 42d and 44a, 44d are depicted in FIG. 15 (these are the marginal rays which define the field of view of the device 10-3 in the plane of the cross section defined by the plane of the paper), it should be apparent that additional similar incident rays originating from the scene 80 are present and follow a path of traversal similar to the rays as described above. An exception is that ray components parallel to the plane of the page undergo deflection by the wedge, while the ones perpendicular to it do not undergo deflection. As such, reference to the incident rays 42a, 42d and 44a, 44d implicitly applies to all such similar incident rays originating from the scene 80 within the field of view.

The objective lens 2 focuses radiation on the detector array 1, after having traversed the wedge-shaped components 5 and 6, to form two simultaneous and separate images of the scene 80 with the background 90, each image being formed on one half of the detector surface. As such, the radiation from the scene 80 and its background 90 is imaged separately and simultaneously onto the detector regions 1a and 1b.

The scene 80 with its background 90 is imaged by the device 10-3 with no moving parts while maintaining a high numerical aperture and low f-number (f/1.5 or less) at the detector array 1. This is accomplished by positioning each of the first and second wedge-shaped components 5 and 6 at a minimum fixed distance d from the objective lens 2 along the optical axis of the device 10-3. Positioning the wedge-shaped components 5 and 6 at a sufficiently large enough distance from the objective lens 2, in combination with the above mentioned deflection angles, allows for the low f-number (high numerical aperture) at the detector array 1 to be maintained. This corresponds to high optical throughput of the device 10-3. As a result, the same radiation from the scene is deflected by the wedge-shaped components 5 and 6 toward the objective lens 2 and imaged on the detector regions 1a and 1b through an f-number of the collection optics 7 which can be maintained close to 1 (f/1) without having to decrease the focal length for increase the aperture diameter D. Accordingly, the minimum distance d which provides such high optical throughput can be approximately lower bounded by:

$$d > \frac{D}{2\tan\left(\frac{\theta}{2}\right)} \quad (5)$$

where D is the aperture diameter of the objective lens and $\theta$ is the vertical field of view of the objective lens.

Having a large numerical aperture (low f-number) provides higher sensitivity of the detector array 1 to the radiation from the scene 80, and less sensitivity to radiation originating from within the internal walls of the device 10-3, the collection optics 7, and the optical components themselves.

As a result of positioning the wedge-shaped components 5 and 6 at the distance d, the vertical fields of view of the wedge-shaped components 5 and 6 are approximately half of the above mentioned vertical field of view of the objective lens 2.

The wedge-shaped components 5 and 6 are preferably positioned symmetrically about the optical axis, such that each is positioned at the same distance d from the objective lens 2, and each is positioned at the same angle relative to the optical axis. Such a design ensures that the same amount of radiation is imaged on the detector regions 1*a* and 1*b* via the objective lens 2 from the wedge-shaped components 5 and 6.

As previously mentioned, the radiation from the scene 80 which is imaged onto the first detector region 1*a* only includes one of the wavelength ranges. The radiation from the scene 80 which is imaged onto the second detector region 1*b* only includes the other one of the wavelength ranges. This is accomplished by positioning the filters 4*a* and 4*b* in the optical train.

In the exemplary implementation shown in FIGS. 14-16, the radiation from the scene 80 imaged on the first detector region 1*a* only includes the in-band radiation from the gas filter 4*a* (i.e., the filter centered at $w_G$), and the radiation from the scene 80 imaged on the second detector region 1*b* only includes the in-band radiation from the flame filter 4*b* (i.e., the filter centered at $w_0$). Accordingly, the first filter 4*a* filters radiation in spectral ranges outside of the first wavelength range (i.e., stop band of the filter centered at $w_G$) and the second filter 4*b* filters radiation in spectral ranges outside of the second wavelength range (i.e., stop band of the filter centered at $w_0$). Thus, the radiation from the scene 80 that is directed by the first wedge-shaped component 5 to be imaged on the first detector region 1*a* includes only the in-band radiation from the gas filter 4*a*, and the radiation from the scene 80 that is directed by the second wedge-shaped component 6 to be imaged on the second detector region 1*b* includes only the in-band radiation from the gas filter 4*a*.

As previously mentioned, the surface of the detector array 1 is divided into the two aforementioned regions by a dividing plane 8 as shown in FIG. 16. FIG. 14 includes a non-limiting exemplary representation of the Cartesian coordinate system XYZ in which the detector plane is parallel to the YZ plane. Accordingly, the dividing plane 8 is parallel to the Z axis and the optical axis is parallel to the X-axis. The wedge-shaped components 5 and 6 are wedge-shaped in the XY plane.

In the embodiment of the device 10-3 shown in FIGS. 14 and 15, the filters 4*a* and 4*b* are not necessarily optical elements from the optics of the collection optics 7, but rather a coating on a first surface 5*a* of the first wedge-shaped component 5 and a first surface 6*a* of the second wedge-shaped component 6, respectively. The first surface 5*a* is the surface of the first wedge-shaped component 5 which is closest to the objective lens 2. Likewise, the first surface 6*a* is the surface of the second wedge-shaped components 6 which is closest to the objective lens 2.

Additionally, a second surface 5*b* of the first wedge-shaped component 5 and a second surface 6*b* of the second wedge-shaped component 6 may be coated with an antireflection coating. The second surfaces 5*b* and 6*b* are the respective surfaces of the wedge-shaped components 5 and 6 which are closest to the scene 80. The antireflection coating provides increased sensitivity of the device to the radiation from the scene 80.

Refer now to FIGS. 18A-18B and 19A, an alternative positioning of the filters 4*a* and 4*b*. Similar to the embodiment of FIGS. 14 and 15, the filters 4*a* and 4*b* are implemented as a coating, but in FIG. 18A the coating is on the second surface 5*b* of the first wedge-shaped component 5. Similarly, in FIG. 18B, the coating is on the second surface 6*b* of the second wedge-shaped component 6. In FIG. 19A the coating is on or near the first and second detector regions 1*a* and 1*b*. Specifically, the first filter 4*a* is implemented as a coating on or near the first detector region 1*a*, and the second filter 4*b* is implemented as a coating on or near the second detector region 1*b*.

Refer now to FIG. 19B, an alternative implementation of the filters 4*a* and 4*b*. In FIG. 19B, the filters 4*a* and 4*b* are implemented as stationary plates positioned in front of, or in direct abutment with, the respective detector regions 1*a* and 1*b*.

In the filter alternatives illustrated in FIGS. 18A and 18B, the first surfaces 5*a* and 6*a* may be coated with an antireflection coating. In the filter alternatives illustrated in FIGS. 19A and 19B, the first and second surfaces of both wedge-shaped components 5 and 6 are preferably coated with an antireflection coating. It is also noted that for clarity of illustration, the thickness of the coating and plates for implementing the filters 4*a* and 4*b* is greatly exaggerated in FIGS. 14, 15, 18A-1B and 19A-19B.

Similar to the devices 10-1, 10-2 and 10-2', the components of the device 10-3 are positioned within a casing defined by internal walls 30 of the device 10-3. Also similar to the devices 10-1, 10-2 and 10-2', the detector array 1 is preferably maintained within a detector case 12.

Figure 17:
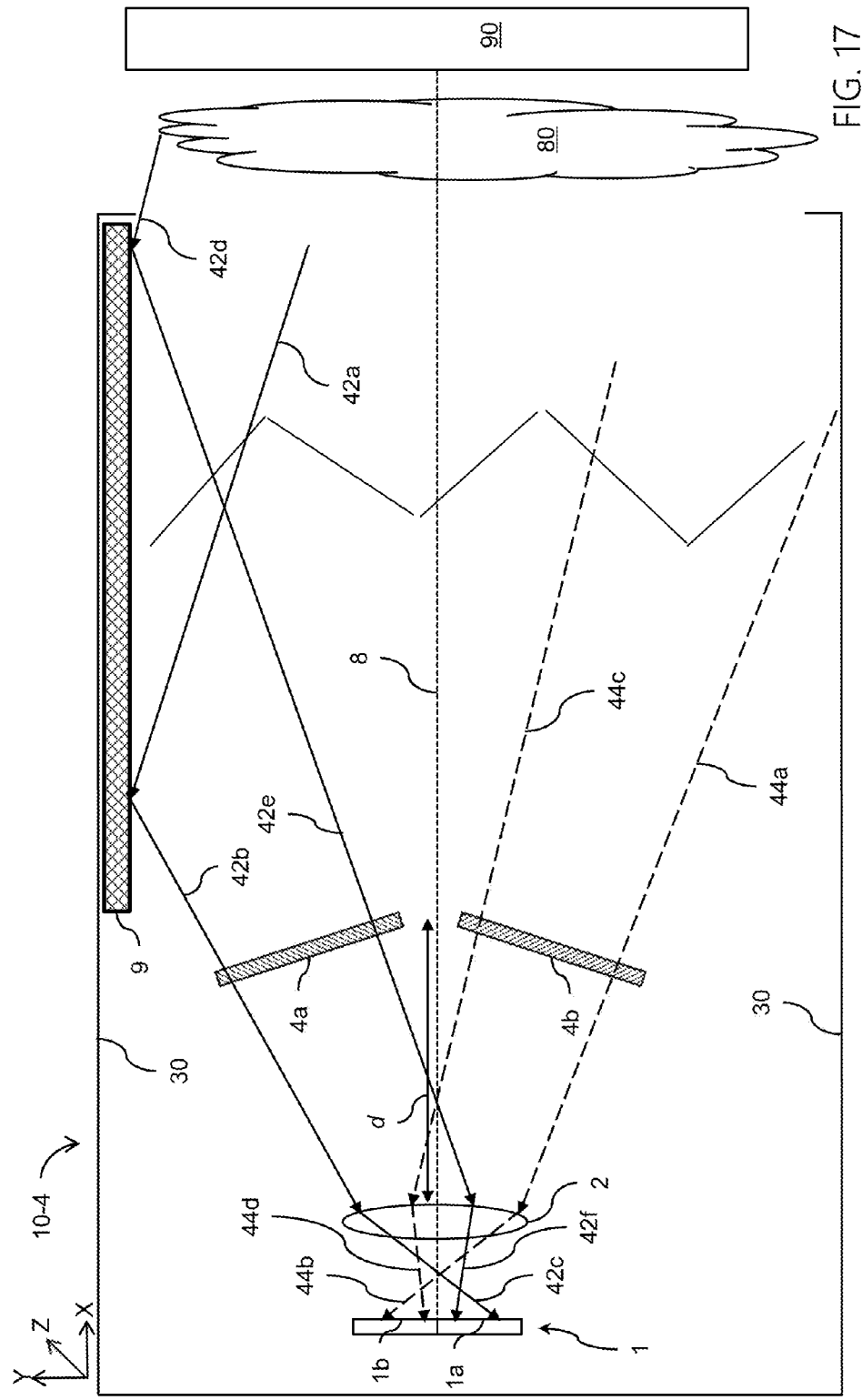
FIG. 17 is a schematic side view illustrating a device with a mirror for detecting and imaging radiation from a scene in two separate wavelength regions without moving parts, according to an embodiment of the invention

3d. Exposure to In-Band and Out-of-Band Filtering by Split Image Mirror Configuration:

A similar result of the device 10-3 may be obtained by using a mirror 9 instead of the two wedge-shaped components 5 and 6 described in the previous section (Section 3c). Such a device 10-4 is shown schematically in FIG. 17. In FIG. 17, the mirror 9 is positioned with respect to the camera system (i.e., detector array 1) such that the reflective surface of the mirror 9 is perpendicular to the plane of the paper (XY plane) and parallel to the optical axis (X axis). Note that the same Cartesian coordinate system XYZ used in FIG. 14 is also used in FIG. 17.

Although not shown in the drawings, the device 10-4 also includes image acquisition electronics 50 similar to the embodiments of the devices 10-1, 10-2 and 10-2', and 10-3 for generating digital signals and for performing computations and algorithms for determining and/or indicating the presence or absence of the gas cloud path concentration distribution and/or flame, as well as imaging and measuring the gas cloud path concentration distribution and/or flame. Furthermore, although not shown in the drawings, the components of the device 10-4 are also positioned within a casing defined by internal walls of the device 10-4 and the detector array 1 is preferably maintained within a detector case, similar to the devices 10-1, 10-2 and 10-2', and 10-3. Note that the objective lens 2 and the two filters 4*a* and 4*b* may be positioned in an optical casing (not shown) of the collection optics which is in turn positioned within the internal walls 30.

FIG. 17 additionally depicts the traversal of incident rays 42*a*-42*f* and 44*a*-44*d* from the scene 80 to the detector array 1, similar to the depiction of the traversal of rays shown in FIG. 15. The properties of the traversal of the rays depicted in FIG. 17 is generally similar to the properties of the traversal of the rays depicted in FIG. 15 unless expressly stated otherwise and will be understood by analogy thereto. Furthermore, the definitions of the field of view of the device 10-4 and the objective lens 2 of the device 10-4 are generally similar to the definitions provided with respect to the device 10-3 and will also be understood by analogy thereto.

The two filters 4*a* and 4*b* are placed either on planes where the two beam bundles are separated (i.e., at the minimum distance d as a function of the aperture diameter of the objective lens and the vertical field of view of the objective lens disclosed in Section 3c and as shown in FIGS.

15 and 17), or directly covering each corresponding region of the detector, similar to the configuration depicted in FIGS. 19A and 19B.

By accordingly positioning the filters 4a and 4b as mentioned above, the device 10-4 maintains a low f-number (f/1.5 or less) at the detector array 1, similar to that of the device 10-3.

Note that a specific property of the traversal of the rays depicted in FIG. 17 that is different from the traversal of the rays depicted in FIG. 15 is lack of the additional reflected rays which pass through the second filter 4b. Specifically, only the first bundle of rays (42a and 42d) is reflected by the mirror 9 before passing through the first filter 4a and the objective lens 2, whereas the second bundle of rays (44a and 44c) is not reflected at all and passes directly through the second filter 4b and the objective lens 2. In other words, the mirror 9 inverts the rays traversing the filter 4a in a vertical upside down direction with respect to the ones of 4b and as a result the two images of the scene 80 formed on the detector array 1 are upside down with respect to each other.

3e. Exposure to In-Band and Out-of-Band Filtering by Specialized Processing of the Detector Array:

As described above, different optical and filtering configurations are presented for exposing the detector pixels to the two band pass filters centered at wavelengths $w_G$ and $w_0$. Among these configurations are pattern filtering techniques using a checkerboard pattern, or alternatively alternating rows or columns of the elements centered at $w_G$ and $w_0$. The filtering result may also be achieved by specialized processing during the manufacturing of the detector array.

FIGS. 21A-21D depict several non-limiting implementations of an embodiment of such a detector array 110. The detector array 110 is processed such that the detector surface that is sensitive to the scene radiation is deposited onto a pre-processed filter substrate 40. For illustration purposes, the detector array 110 is depicted as including a surface 110a that is sensitive to the scene radiation. The filter substrate 40 has the appropriate spectral characteristics of the two band pass filters centered at wavelengths $w_G$ and $w_0$. The filter substrate 40 is preferably pre-processed (i.e., manufactured) according to the patterns described in Section 3b. Specifically, the filter substrate 40 may be implemented in a checkerboard pattern (FIG. 10), alternating rows of the elements centered at $w_G$ and $w_0$ (FIG. 11), or alternating columns of the elements centered at $w_G$ and $w_0$ (not shown). Accordingly, each of the filter substrate elements 40a-1, 40a-2, ..., 40a-N, 40b-1, 40b-2, ..., 40b-N covers a respective elements of the detector array 110.

The pre-processed filter substrate 40 may be manufactured according to any reasonable technique, such as, for example, the technique described in "Process Technology to Integrate Polycrystalline Uncooled PbSe Infrared Detectors on Interference Filters", by M. T. Rodrigo et al., SPIE Proceedings Vol. 5251, p. 97, 2004.

FIG. 21A is an exploded view of the resulting detector surface 110a deposited onto the pre-processed filter substrate 40 in which the filter substrate 40 has a checkerboard pattern. FIG. 21B is a top view of the detector surface 110a deposited onto the pre-processed filter substrate 40 in which the filter substrate 40 has a checkerboard.

FIG. 21C is an exploded view of the resulting detector surface 10a deposited onto the pre-processed filter substrate 40 in which the filter substrate 40 has alternating rows of the elements centered at $w_G$ and $w_0$. FIG. 21D is a side view of the detector surface 110a deposited onto the pre-processed filter substrate 40 in which the filter substrate 40 has alternating rows of the elements centered at $w_G$ and $w_0$.

Alternatively, the filter substrate 40 may be implemented such that the filter substrate 40 covers half of the detector array 110 uniformly with elements centered at $w_G$ and the other half of the surface of the detector array 110 uniformly with elements centered at $w_0$. In such an implementation, the detector array 110 can be considered as having two separate equally sized detector regions, similar to the detector arrays of the devices 10-3 and 10-4 previously described. As should be apparent, the two detector regions are effectively separated by the plane of the optical axis.

FIGS. 21E and 21F are an exploded view and side view of such an implementation, respectively. As in FIGS. 21A-21D, the detector surface 110a is deposited onto the pre-processed filter substrate 40.

Note that in FIGS. 21A-21F, similar to FIGS. 10 and 11, the white squares 40a-1, 40a-2, ..., 40a-N correspond to the filter elements centered at $w_G$ and the diagonally hatched squares 40b-1, 40b-2, ..., 40b-N correspond to filter elements centered at $w_0$.

The detector array 110 implementation shown in FIGS. 21E and 21F is preferably used as a replacement for the detector array 1 and filters 4a and 4b of the split image configurations of the devices 10-3 (Section 3c) and 10-4 (Section 3d). The detector array 110 implementation shown in FIGS. 21A-21D is preferably used as a replacement for the detector array 1 and the patterned filter 4 of the device 10-2' (Section 3b). It is also noted that for clarity of illustration, the thicknesses of the detector surfaces and the filter substrate are greatly exaggerated in FIGS. 21A-21F.

Note also that in the above described implementations of the detector array 110, the filter substrate 40 should be deposited relative to the detector surface such that the filter substrate elements centered at $w_G$ and $w_0$ (40a-1, 40a-2, ..., 40a-N, 40b-1, 40b-2, ..., 40b-N) match the shape, pitch and position of the respective detector elements.

In the non-limiting implementations of the embodiment of the detector array 110 illustrated in FIGS. 21A-21F, a total of 2N filter elements are depicted, with each wavelength region ($w_G$ and $w_0$) having N filter elements.

The above described non-limiting implementations of the detector array 110 embodiments require specially processed and manufactured filter substrates. Therefore, it may be desirable to avoid specialized manufacturing and the use of such filters altogether. Accordingly, the detector array may be manufactured such that roughly half of the individual detector elements (i.e., pixels) are sensitive to wavelengths $w_G$ and the other roughly half of the detector elements are sensitive to wavelengths $w_0$. In other words, the detector array is manufactured such that half of the detector pixels are sensitive to wavelengths in a spectral range corresponding to the in-band spectral range and the other half of the detector pixels are sensitive to wavelengths in a spectral range corresponding to the out-of-band spectral range. The two different sensitivities may be achieved, for example, by doping the semiconductor material of the detector array in two different stoichiometries. Note that additional processes may be carried out in addition to the doping in order to ensure that the two resultant spectral ranges have minimal or no spectral overlap.

FIGS. 22A-22C depict several non-limiting implementations of an embodiment of a detector array 120 with half of the individual detector elements sensitive to wavelengths $w_G$ and the other half of the detector elements sensitive to wavelengths $w_0$. Similar to FIGS. 10 and 11, in such implementations the white squares represent the detector pixels that are doped to be sensitive to wavelengths $w_G$ (120a-1, 120a-2, ..., 120a-M), and the diagonally hatched squares represent the detector pixels that are doped to be sensitive to wavelengths $w_O$ (120b-1, 120b-2, ..., 120b-M).

The detector semiconductor material may be doped such that the resultant detector pixels are arranged in a checkerboard pattern (FIG. 22A), alternating rows of detector pixels sensitive to $w_G$ and $w_O$ (FIG. 22B), alternating columns of detector pixels sensitive to $w_G$ and $w_O$ (not shown), or with half of the detector pixels uniformly sensitive to $w_G$ and the other half of the detector pixels uniformly sensitive to $w_O$ (FIG. 22C). Note that as in the implementation of FIGS. 21E and 21F, the implementation of FIG. 22C is used as a replacement for the detector array 1 and filters 4a and 4b of the split image configurations of the devices 10-3 (Section 3c) and 10-4 (Section 3c).

In the non-limiting implementations of the embodiment of the detector array 120 illustrated in FIGS. 22A-22C, a total of 2M detector pixels (i.e. detector elements) are depicted, with M of the detector pixels being sensitive to $w_G$ and M of the detector pixels being sensitive to $w_O$.

Figure 24:
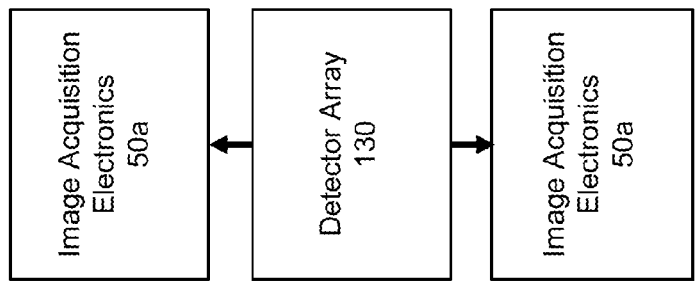
FIG. 24 is a block diagram of two sets of image acquisition electronics coupled to the detector array of FIG. 23.

Alternatively, the detector array may be manufactured such that individual detector elements are sensitive to wavelengths in both $w_G$ and $w_O$. Refer to FIG. 23, an embodiment of such a detector array 130. The detector array 130 includes a plurality of detector elements 130a, 130b, ..., 130N. Each detector element includes two sub-elements (a first set of sub-elements 130a-1, 130b-1, ..., 130N-1, and a second set of detector sub-elements 130a-2, 130b-2, ..., 130N-2). The first set of detector sub-elements 130a-1, 130b-1, ..., 130N-1 are sensitive to $w_G$, and the second set of detector sub-elements 130a-2, 130b-2, ..., 130N-2 are sensitive to $w_O$. As shown in FIG. 24, instead of the detector array being coupled to a single image acquisition electronics 50 as previously described, the detector array 130 of FIG. 23 is coupled to two sets of image acquisition electronics (first image acquisition electronics 50a and second image acquisition electronics 50b). Specifically, the first image acquisition electronics 50a is coupled to the first set of sub-elements 130a-1, 130b-1, ..., 130N-1, and the second image acquisition electronics 50b is coupled to the second set of sub-elements 130a-2, 130b-2, ..., 130N-2.

In the non-limiting example embodiments of the detector array 130 illustrated in FIG. 23, a total of 2N detector sub-elements are depicted, with N of the detector sub-elements being sensitive to $w_G$ and N of the detector sub-elements being sensitive to $w_O$. Similar to FIGS. 10 and 11, the white detector sub-elements represent the detector sub-elements sensitive to $w_G$ (130a-1, 130b-1, ..., 130N-1), and the diagonally hatched detector sub-elements represent the detector sub-elements that are sensitive to $w_O$ (130a-2, 130b-2, ..., 130N-2).

Accordingly, the outputs of the individual detector elements are processed by the appropriate image acquisition electronics in order to generate and record signals corresponding to the detector elements (i.e., pixels) for imaging the scene 80. As a result, the radiation from the scene that is imaged onto the detector array 130 can be reconstructed for both wavelength sensitivities $w_G$ and $w_O$.

As depicted in FIG. 23, the detector sub-elements are shown as rectangular in shape, in which the sub-elements that are sensitive to $w_G$ are positioned to the left of the corresponding sub-element sensitive to $w_O$, relative to the detector plane. Note that although FIG. 23 depicts the detector sub-element shapes as generally rectangular in the vertical direction relative to the detector plane, the detector sub-elements may also be generally rectangular in the horizontal direction relative to the detector plane. Accordingly, the detector sub-elements of a detector element may be generally rectangular in the vertical direction relative to the detector plane, while the detector sub-elements of a neighboring detector element may be generally rectangular in the horizontal direction relative to the detector plane.

Furthermore, the relative left-right vertical positioning of a single detector element may be different from the relative positioning of detector sub-elements of a neighboring detector element. For example, each detector element in an odd numbered row may have the detector sub-element sensitive to $w_G$ positioned to the left of the respective detector sub-element sensitive to $w_O$, and each detector element in an even numbered row may have the detector sub-element sensitive to $w_G$ positioned to the right of the respective detector sub-element sensitive to $w_O$. As such, a vertical rectangular checkerboard pattern may be formed. Similarly, if using detector sub-elements that are generally rectangular in the horizontal direction relative to the detector plane, the relative up-down horizontal positioning of a single detector element may be different from the relative positioning of detector sub-elements of a neighboring detector element in order to form a horizontal rectangular checkerboard pattern.

It is noted herein that different detector sub-element shapes can be used, so long as the two sets of detector sub-elements have different spectral responses (i.e., one set of sub-elements is sensitive to $w_G$ and the other set of sub-elements is sensitive to $w_O$). Preferably, the detector sub-elements of a single detector element are of approximately the same size in order to evenly partition a detector element into two detector sub-elements of approximately equal area. Also note that in practice there may be gaps between two sub-elements of a single detector element, however for clarity of illustration no gaps are shown in FIG. 23.

It is noted herein that the term "detector sub-element" may also be interpreted in other words as "detector element region", "region of detector element", "detector element zone", and "zone of detector element". For example, the detector sub-elements 130a-1 and 130a-2 can also be referred to as a first region 130a-1 of the detector element 130a and a second region 130a-2 of the detector element 130a.

Note that the detector array 130 implementation of FIG. 23 is preferably used as a replacement for the detector array 1 and the patterned filter 4 of the device 10-2' (Section 3b). Also note that the description herein of the structure, components, and operation of each set of image acquisition electronics 50a and 50b is generally similar to that of the image acquisition electronics 50, and will be understood by analogy thereto.

4. Drift Correction:

For each of the embodiments of the devices 10-1, 10-2, 10-2', 10-3, and 10-4 discussed above in Sections 3a-3d, as well as the variations of these embodiments when combined with the detector and filtering combinations discussed in Section 3e, changes in the environmental temperature surrounding these devices causes the emission of radiation originating from within the internal walls 30 of the device, the optical casing, and the optical components themselves to vary with time. This emission of radiation is referred to interchangeably as unwanted radiation. The unwanted radiation in turn leads to drifts in the imaged pixels signals, and erroneous results in the gas path concentration or flame measurement of each pixel of the image of the scene as measured by the devices according to appropriate algorithms.

In the subsequent sections of this description, variations of the devices 10-2 and 10-4 discussed in Sections 3a-3e will be presented in order to explain the drift correction methodology of the present disclosure. Each of the variations of these devices further operates to reduce the effect of the unwanted radiation in order to ensure accuracy of the imaging, detection and measurement functionality previously described. In other words, each of the variations of these devices is operative to allow compensation for the signal drift resulting from the unwanted radiation. Ideally, the signal drift reducing devices are operative to reduce the signal drift to a negligible amount essentially correcting for the effect of the drift, so that the device may provide accurate results. Accordingly, the terms "correcting for", "compensating for" and "reducing", when applied to drift in imaged pixels signals, are used interchangeably herein.

Note that although only variations of the devices 10-2 and 10-4 are presented, these serve as non-limiting examples for providing explanation as to the drift correction methodology of the present disclosure, and similar variations can be made to the devices 10-1, 10-2', and 10-3 to achieve analogous results.

As will be discussed, the image acquisition electronics 50 of each device is further configured to apply a correction to the generated scene pixels signals in order to reduce the drift in the generated scene pixels signals caused by the radiation originating from within the internal walls 30, the optical casing (i.e., collection optics), and the optical components themselves.

Refer now to FIG. 25, a device 100-2 for reducing signal drift according to an embodiment of the present disclosure. As should be understood, the description of the structure and operation of the device 100-2 is generally similar to that of the device 10-2 unless expressly stated otherwise, and will be understood by analogy thereto. Two specific features of the device 100-2 are different from the device 10-2. Firstly, the detector array 1 of the device 100-2 is partitioned into two separate detector regions (a first detector region 1a and a second detector region 1b). The area of the second detector region 1b is significantly smaller or not usually larger than the area of the first detector region 1a and can be visualized as a strip (or part of a strip, or a single pixel in the center or within region 1b) extending across the top or bottom of the detector plane (i.e., the surface of the detector array that is sensitive to the scene radiation).

FIG. 26 is a front view of the detector 1 illustrating an implementation in which the second detector region 1b is a strip extending across the top of the detector plane. The second detector region 1b can also be shaped as a square or shorter rectangle than as shown in FIG. 26, and placed anywhere along the region shown in FIG. 26.

Returning to FIG. 25, the device 100-2 images the scene in the same way as the device 10-2 while projecting infrared radiation emitted by a surface 60 (e.g. a blackbody radiation source) onto the second detector region 1b. As will be discussed in more detail in subsequent sections of the present disclosure, a temperature probe 62 is placed in proximity to, or within, the surface 60. The surface 60 is stationary (contrary to the two alternating filters driven by the motor 3) and in good thermal contact with a portion of the filter 4, and is in the vicinity of the optical components, so that the temperature of the surface 60 can be assumed to be at all times close to the temperature of the optics and follow closely the temperature of the device walls 30 and collection optics 7, which in turn is affected by (and usually, especially when used in outdoor conditions, close to) the environment temperature. Note that alternatively, the surface 60 can be placed in good thermal contact directly with the device walls 30. In other words, the signals of the detector elements of the second detector region 1b do not carry information from the scene, but rather carry information on the self-emitted radiation of the internal walls 30 and collection optics 7 of the device. Therefore, the pixels signals of the second detector region 1b can be used by the device 100-2 algorithms and electronics to correct for the unwanted changes to the signals of the first detector region 1a that are caused by changing environment and not by the corresponding regions of scene. The pixels of the second detector region 1b are referred to as "blind pixels". Additionally, a baffle or baffles may be positioned (if needed) to prevent radiation from the scene from reaching the second detector region 1b.

The above explanation constitutes a second specific feature of the device 100-2 which is different from the device 10-2, namely the inclusion of the blackbody radiation source 60 close to the optical elements and within the internal walls 30 of the device 100-2. The blackbody radiation source 60 is positioned such that the blackbody radiation source 60 emits radiation which is projected only onto the second detector region 1b, resulting in the blind pixels as previously mentioned to produce signals which, as will be discussed in more detail below, are used to reduce the drift in the signals from the scene, due to changing case and optics self-emission. The traversal of incident rays 64a-64d from the blackbody radiation source 60 to the detector array 1 is shown in FIG. 25. Also shown for completeness in FIG. 25 is the traversal of incident rays 42a-42f from the scene onto the detector array 1. For clarity of illustration, the incident rays from the blackbody radiation source 60 are depicted with dashed arrows, whereas the incident rays from the scene are depicted with solid arrows.

The blackbody radiation source 60 can be placed in various positions within the device 100-2. Preferably, the blackbody radiation source 60 is placed at an intermediate focal plane of the device 100-2 between the objective lens 2 and the re-imaging optical lens 9, and most preferably in contact with the filter 4 or the filter holder. The placement of the blackbody radiation source 60 within the imaging device 100-2 is incumbent upon the radiation being projected onto only the second detector region 1b to generate the blind pixels signals.

In the non-limiting implementation of the imaging device 100-2 shown in FIG. 25, the blackbody radiation source 60 is positioned such that the radiation from the blackbody radiation source 60 is directed through the re-imaging optical lens 9 onto the second detector region 1b which is located at the top of the detector plane. Note that in addition to the blackbody radiation source 60, an additional blackbody radiation source can be placed in a symmetric position about the optical axis such that the radiation from the additional blackbody radiation source is projected through the re-imaging lens 9 onto a third detector region located at the bottom of the detector plane (i.e., as a strip or part of a strip in a symmetric position relative to the second detector region 1b).

Figure 27:
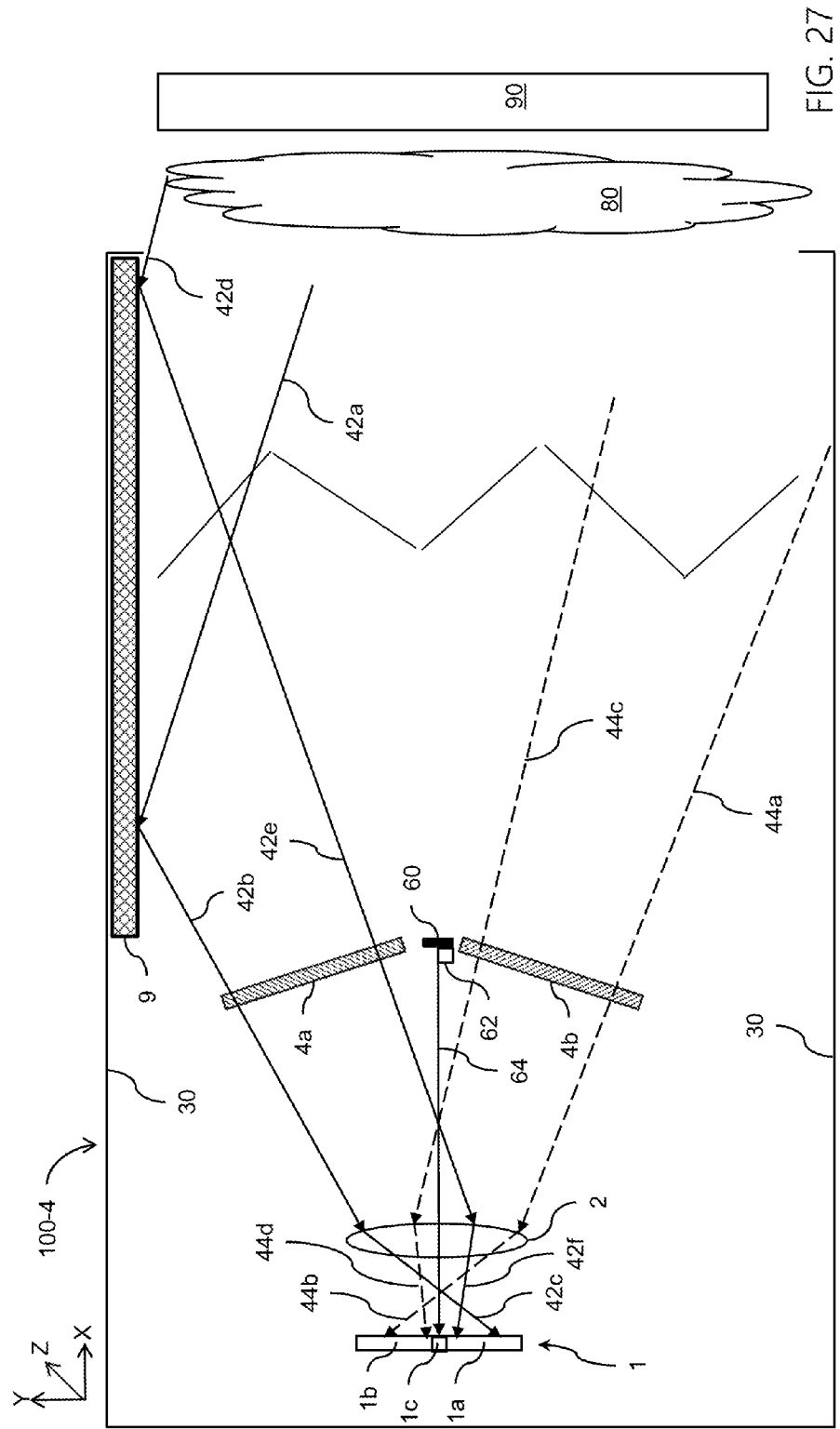
FIG. 27 is a schematic side view illustrating an alternative device for drift correction according to an embodiment of the invention.

Refer now to FIG. 27, a device 100-4 for reducing signal drift according to an embodiment of the present disclosure. As should be understood, the description of the structure and operation of the device 100-4 is generally similar to that of the device 10-4 unless expressly stated otherwise, and will be understood by analogy thereto. Similar to the device 100-2, two specific features of the device 100-4 are different from the device 10-4. Firstly, the detector array 1 of the device 100-4 is partitioned into three separate detector regions (a first detector region 1a, a second detector region 1b, and a third detector region 1c). The area of the third detector region 1c is significantly smaller or not usually larger than the areas of the other two detector regions and can be visualized as a strip extending across the center of the detector plane along the Z-axis (i.e., the surface of the detector array that is sensitive to the scene radiation).

FIG. 28A is a front view of the detector 1 illustrating an implementation in which the third detector region 1c is a strip extending across the center of the detector plane, and is a variation of the depiction of the detector array shown in FIG. 16.

Returning to FIG. 27, the device 100-4 images the scene in the same way as the device 10-4 while projecting infrared radiation emitted by a surface 60 (e.g. a blackbody radiation source) onto the third detector region 1c. As will be discussed in more detail in subsequent sections of the present disclosure, a temperature probe 62 is placed in proximity to, or within, the surface 60. The surface 60 is in good thermal contact with the collection optics of the device and is in the vicinity of the collection optics, so that, similar to the device 100-2, the temperature of the surface 60 can be assumed to be at all times close to the temperature of the collection optics (i.e., objective lens 2 and filters 4a and 4b), and closely following the temperature of the device walls 30 which in turn is affected by (and usually, especially when used in outdoor conditions, close to) the environment temperature. In other words, the signals of the detector elements of the third detector region 1c do not carry information from the scene, but rather carry information on the self-emitted radiation of the collection optics of the device and internal walls 30. Therefore, the pixels signals of the third detector region 1c can be used by the device 100-4 algorithms and electronics to correct for the unwanted changes to the signals of the detector regions 1a and 1b that are caused by changing environment and not by the corresponding regions of scene. Similar to the above description of the device 100-2, the pixels of the third detector region 1c are referred to as "blind pixels", and a baffle or baffles may be positioned (if needed) to prevent radiation from the scene from reaching the third detector region 1c.

The above explanation constitutes a second specific feature of the device 100-4 which is different from the device 10-4, namely the inclusion of the blackbody radiation source 60 within the collection optics of the imaging device 100-4. The blackbody radiation source 60 is positioned along the optical axis between the two filters 4a and 4b such that the blackbody radiation source 60 emits radiation which is projected only onto the third detector region 1c, resulting in the blind pixels as previously mentioned to produce signals which, as will be discussed in more detail below, are used to reduce the drift in the signals from the scene, due to changing case and optics self-emission.

Since the blackbody radiation source 60 is positioned along the optical axis between the two filters 4a and 4b, the main incident ray 64 from the blackbody radiation source 60 passes through the center of the objective lens 2 and is not deflected by the objective lens 2, allowing for the incident ray 64 to reach the center of the detector array 14 as shown in FIG. 27.

The placement of the blackbody radiation source 60 within the imaging device 100-4 is incumbent upon the radiation being projected by the objective lens 2 onto only the third detector region 1c to generate the blind pixels signals.

The methodology for reducing signal drift will now be presented with reference to both of the devices 100-2 and 100-4. Throughout this section, the enumeration 100-X is taken to refer to either or both of the devices 100-2 and 100-4. In situations where a specific process step for signal drift correction is unique to one of the devices 100-2 or 100-4, the enumeration of the specific device 100-2 or 100-4 will be used. The process of reducing and/or correcting for the drift in the generated scene pixels signals is applied to all scene pixels signals. For clarity, the process will be explained with reference to correcting for the drift in a single scene pixel signal as an example, and applied to all the other pixels in the same way.

The individual optical components, the optical casing (when present), and the spaces between the internal walls 30 of the device 100-X are assumed to be at a temperature $T_E$, which is usually close to and affected by the temperature of the environment in which the device 100-X operates. As a result, the amount of radiation originating from the individual optical components and the optical casing is a direct function of the temperature $T_E$.

Since the blackbody radiation source 60 or sources in the case of the device 100-2) is placed within the device 100-X and in good thermal contact with the device 100-X, the optical components, optical casing and the walls 30, the temperature of the blackbody radiation source 60 ($T_{BB}$) is assumed to be the same or a function of the temperature $T_E$ (i.e. $T_{BB}$ and $T_E$ are correlated). $T_{BB}$ can be measured by a temperature probe 62 placed in proximity to, or within, the blackbody radiation source 60.

A measured scene pixel signal S from a region of the scene, can be expressed as the sum of two signal terms, a first signal term $S_O$, and a second signal term $S_S$. The first signal term $S_O$ is the signal contribution to S corresponding to the radiation originating from the optical components, the optical casing, and walls 30 of the device 100-X. The second signal term $S_S$ is the signal contribution to S due to the radiation originating from the corresponding region of the scene imaged on the pixel in question. Accordingly, the scene pixel signal S is the result of the combination of radiation originating from the device walls 30 and environment, optical components and the optical casing, and radiation from the scene, being imaged onto the detector region(s) not associated with the blind pixels (i.e., the first detector region 1a of the device 100-2, and the two detector regions 1a and 1b of the device 100-4).

Since the blackbody radiation source 60 is assumed to be at a temperature that is a direct function of the temperature $T_E$, the radiation emitted by the blackbody radiation source 60 is representative of the radiation originating from the optical components, the optical casing, the device walls 30 and environment. Accordingly, a blind pixel signal, $S_B$, may be assumed to be also a good representation of the contribution to the scene pixel signal due to the radiation originating from the environment, the optical components and the optical casing.

As a result of the radiation originating from the optical components and the optical casing being a direct function of the temperature $T_E$, the first signal term $S_O$ (if the above assumptions are correct) is also a direct function of the temperature $T_E$. This can be expressed mathematically as $S_O=f_1(T_E)$, where $f_1(\bullet)$ is a function.

Similarly, as a result of the blind pixel signal $S_B$ being assumed to be a good representation of the pixel signal contribution corresponding to the radiation originating from the optical components and the optical casing, the blind pixel signal $S_B$ can also be assumed to be a direct function of the walls 30, the environment and optical system temperature $T_E$. This can be expressed mathematically as $S_B=f_2(T_E)$, where $f_2(\bullet)$ is also a function.

Accordingly, since both the first signal term $S_O$ and the blind pixel signal $S_B$ are functions of the same operating temperature $T_E$, it is conceivable that a correlation may exist between the first signal term $S_O$ and the blind pixel signal $S_B$. With the knowledge of the correlation (if existing), the first signal term $S_O$ and the changes in time of $S_O$ (referred to hereinafter as "scene pixel signal drifts") can be determined from the blind pixel signal $S_B$ and the changes in time of $S_B$. Accordingly, in the above assumptions, the changes in time or drifts of the scene pixel signal $S$ due to environment status can be removed and corrected for, in order to prevent gas and/or flame quantity calculation errors.

In the context of this document, the term "correlation", when applied to a relationship between sets of variables or entities, generally refers to a one-to-one relationship between the sets of variables or entities. As such, a correlation between the first signal term $S_O$ and the blind pixel signal $S_B$ indicates a one-to-one relationship between the first signal term $S_O$ and the blind pixel signal $S_B$ at any temperature of the device 100-X. This correlation is determined by a sequence of controlled measurements. The sequence of controlled measurements is performed prior to when the device 100-X is in operation in the field, and can be considered as a calibration procedure or process to be performed in manufacturing of the device. For the purposes of this disclosure, the device 100-X is considered to be in an operational stage when the radiation from the scene is imaged by the detector array 1 and the drift in the generated imaged pixels signals is actively reduced by the techniques as will later be described.

Recall the assumption that the blackbody radiation source 60 is at a temperature that is a direct function of the temperature $T_E$. According to this assumption, the blind pixel signal $S_B$ is assumed to be a good representation of the pixel signal contribution due to the radiation originating from the optical components and the optical casing. Prior to determining the correlation function between the first signal term $S_O$ and the blind pixel signal $S_B$, it is first necessary to verify the actuality of the above assumptions. Subsequent to the verification, the correlation function between the time changes of the first signal term $S_O$ (scene pixel signal drifts) and the blind pixel signal $S_B$ time changes can be determined. Both the verification process, and the process of determining the correlation function, is typically conducted through experiment. In practice, only drifts, or unwanted changes of the imaged pixel signals over time are to be corrected for, so the process of verification and determination of the correlations are only needed and performed between the differentials of $S_O$, $S_B$, or variations during time due to environment temperature variations.

Figure 29:
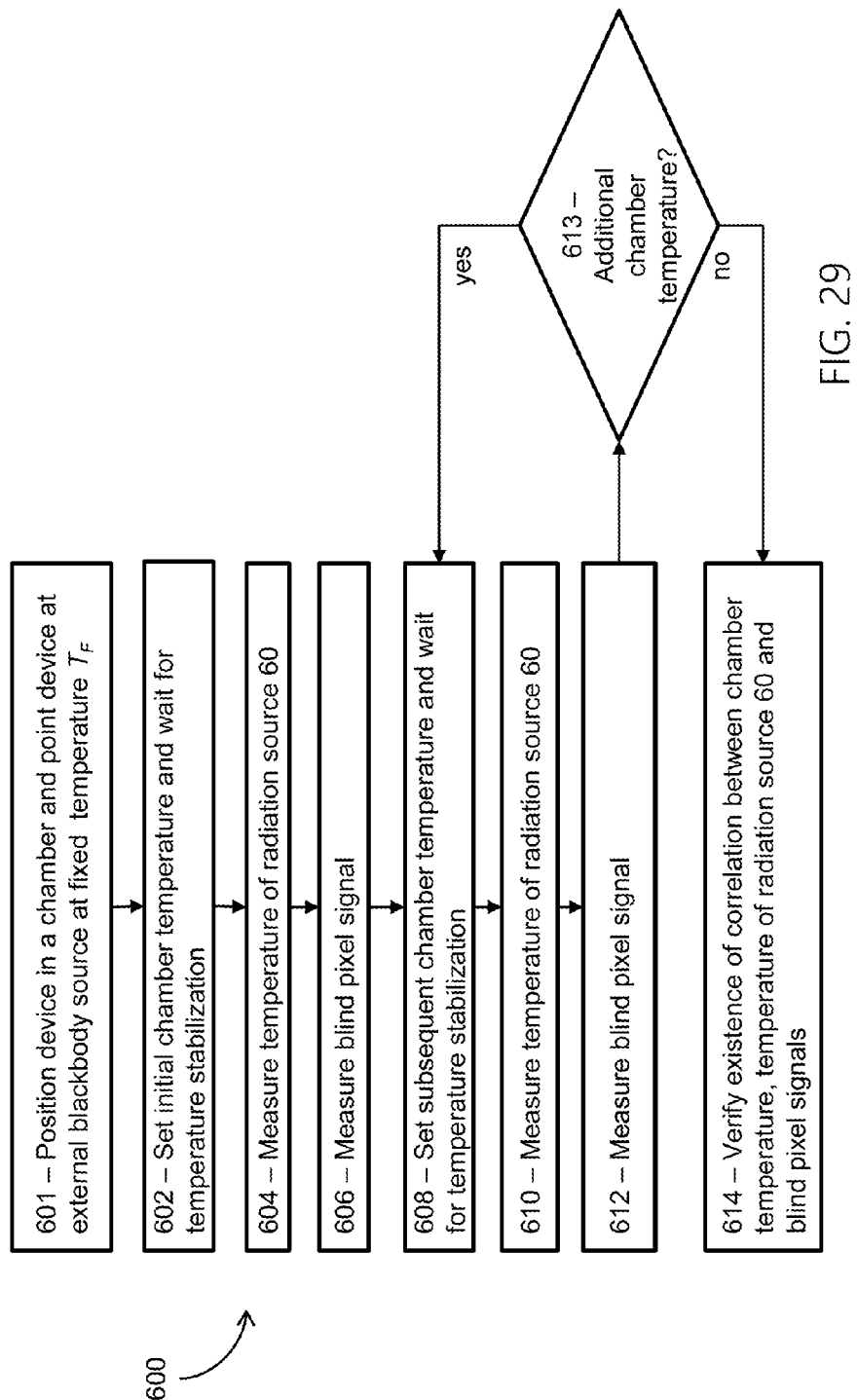
FIG. 29 is a flowchart for verifying a correlation according to an embodiment of the invention.

Refer now to FIG. 29, a flowchart of a process 600 for verifying the existence of a correlation between the environment temperature, the temperature of the blackbody radiation source 60 (or sources in the case of the device 100-2) and the blind pixel signal $S_B$. In step 601, the device 100-X is placed in a temperature controlled environment, such as a temperature chamber having a controllable and adjustable temperature, and to point the device 100-X at an external blackbody source at a fixed temperature $T_F$ so that the scene pixels of the detector region(s) not associated with the blind pixels (i.e., the first detector region 1a of the device 100-2, and the two detector regions 1a and 1b of the device 100-4) are exposed to unchanging radiation from the external blackbody. Such an external blackbody source is used in place of the scene. In step 602, the temperature of the temperature chamber is set to an initial temperature $T_0$. The temperature of the temperature chamber and the imaging device 100-X are let to stabilize to temperatures $T_0$ and $T_E$ respectively by allowing for an appropriate interval of time to pass.

Once the temperatures have stabilized, $T_{BB}$ (which may be practically equal to $T_E$) is measured via the temperature probe 62 in step 604. In step 606, the blind pixel signal $S_B$ is measured via the image acquisition electronics 50. Accordingly, the blind pixel signal $S_B$ and $T_{BB}$ are measured at temperature $T_0$ in steps 604 and 606, respectively.

In step 608, the temperature of the temperature chamber is set to a different temperature $T_1$. Similar to step 602, the temperatures of the temperature chamber and the device 100-X are let to stabilize to temperature $T_1$ and a new temperature $T_E$, respectively, by allowing for an appropriate interval of time to pass. Once the temperatures have stabilized, $T_{BB}$ is measured via the temperature probe 62 in step 610. In step 612, the blind pixel signal $S_B$ is measured via the image acquisition electronics 50. Accordingly, the blind pixel signal $S_B$ and $T_{BB}$ are measured at chamber temperature $T_1$ in steps 610 and 612, respectively.

The process may continue over a range of chamber temperatures of interest, shown by the decision step 613. For each selected chamber temperature, the blind pixel signal $S_B$ and $T_{BB}$ and $T_E$ are measured as in steps 604, 606, 610 and 612 above.

In step 614, the existence of a correlation between the environment temperature, the blind pixel signal $S_B$ and the temperature of the blackbody radiation source 60 (or sources in the case of the device 100-2) is verified by analyzing the resultant measurements. For example, the blind pixel signal $S_B$ measurements from steps 604 and 610 can be plotted as function of the operating temperatures $T_E$ established in steps 602 and 608. Similarly, the $T_{BB}$ measurements from steps 606 and 612 can be plotted or otherwise visualized versus the range of operating temperatures $T_E$ established in steps 602 and 608. An example of plots for executing step 614 is depicted in FIGS. 32A and 32B.

Figures 32A, 32B:
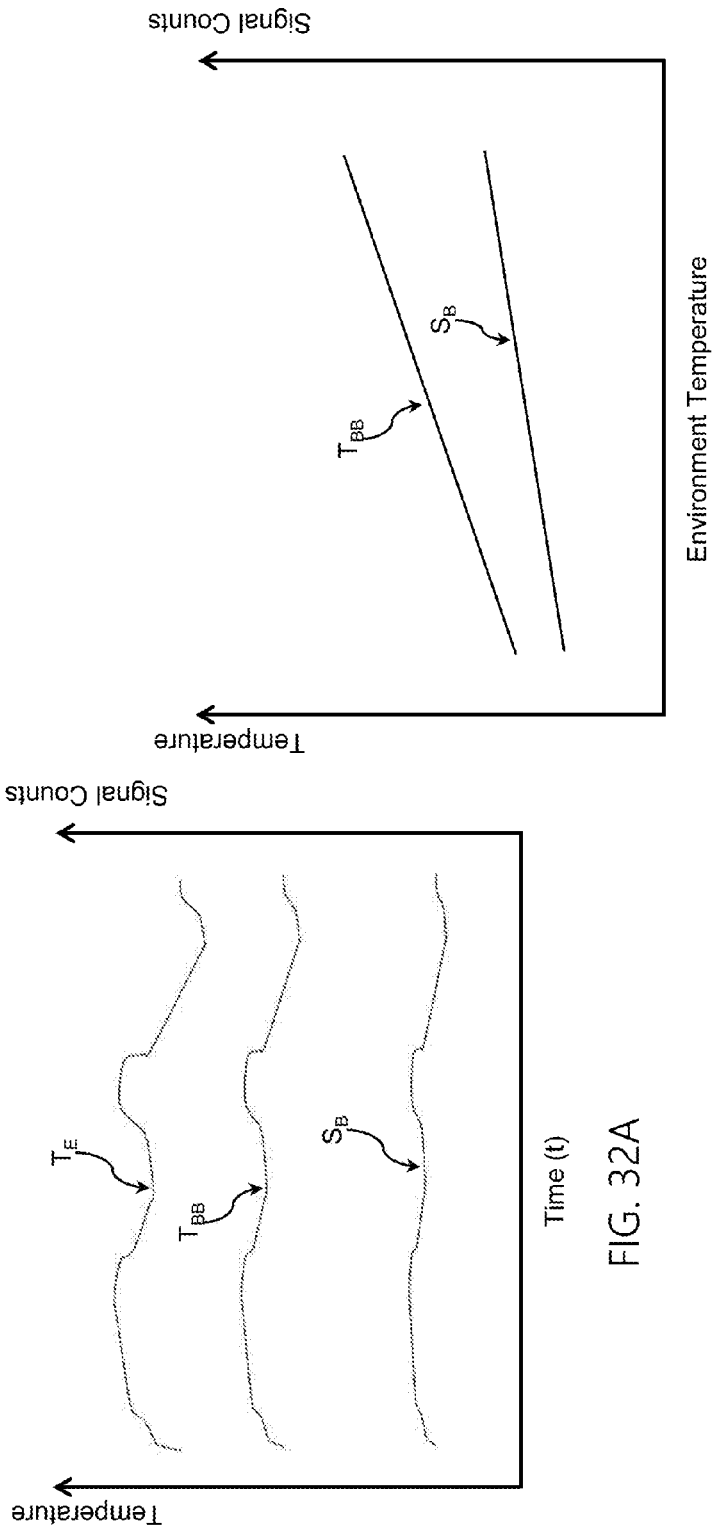
FIGS. 32A and 32B show examples of plots used for performing steps of the flowchart of FIG. 29.

Referring first to FIG. 32A, an example of plots of the measurements of the operating temperatures ($T_E$), the blind pixel signal ($S_B$), and the blackbody radiation source temperature ($T_{BB}$ measured via the temperature probe 62) is depicted. The plots shown in FIG. 32A are intended to serve as illustrative examples, and should not be taken as limiting in the scope or implementation of the process 600.

Note that the x-axis in FIG. 32A is designated as "time (t)", as should be apparent due to the variation of the operating temperatures ($T_E$) as time (t) goes by. Also note that the example plots shown in FIG. 32A includes two y-axes. The first y-axis (shown on the left side of FIG. 32A) is designated as "temperature" and corresponds to the operating temperatures ($T_E$) and the blackbody radiation source temperature ($T_{BB}$). The second y-axis (shown on the right side of FIG. 32A), is designated as "signal counts" and is the measured output of the ADC 52 corresponding to the blind pixel signal ($S_B$).

If there is a linear (or any other one-to-one) relationship between the three entities $T_E$, $T_{BB}$, and $S_B$, the above discussed assumptions are upheld to be valid, and therefore there exists a correlation between the temperatures $T_E$, $T_{BB}$, and the blind pixel signal $S_B$.

Referring now to FIG. 32B, the recognition of such a linear relationship can be shown by alternatively plotting the measurements depicted in FIG. 32A. As should be apparent, the example plots shown in FIG. 32B show the blackbody radiation source temperature ($T_{BB}$) and the blind pixel signal ($S_B$) signal counts versus the temperature $T_E$, which, as previously discussed, is the environment temperature.

Accordingly, the x-axis in FIG. 32B is designated as "environment temperature". As in FIG. 32A, FIG. 32B also includes two y-axes. The first y-axis (shown on the left side of FIG. 32B) is designated as "temperature" and corresponds to the blackbody radiation source temperature ($T_{BB}$). The second y-axis (shown on the right side of FIG. 32B), is designated as "signal counts" and is the measured output of the ADC 52 corresponding to the blind pixel signal ($S_B$).

Similar to the plots shown in FIG. 32A, the plots shown in FIG. 32B are intended to serve as illustrative examples, and should not be taken as limiting in the scope or implementation of the process 600. As can be clearly seen in the illustrative example depicted in FIG. 32B, a linear relationship of non-zero slope (which is an example of a one-to-one relationship) exists between the three entities $T_E$, $T_{BB}$, and $S_B$, thus implying that the three entities are correlated.

Figure 30:
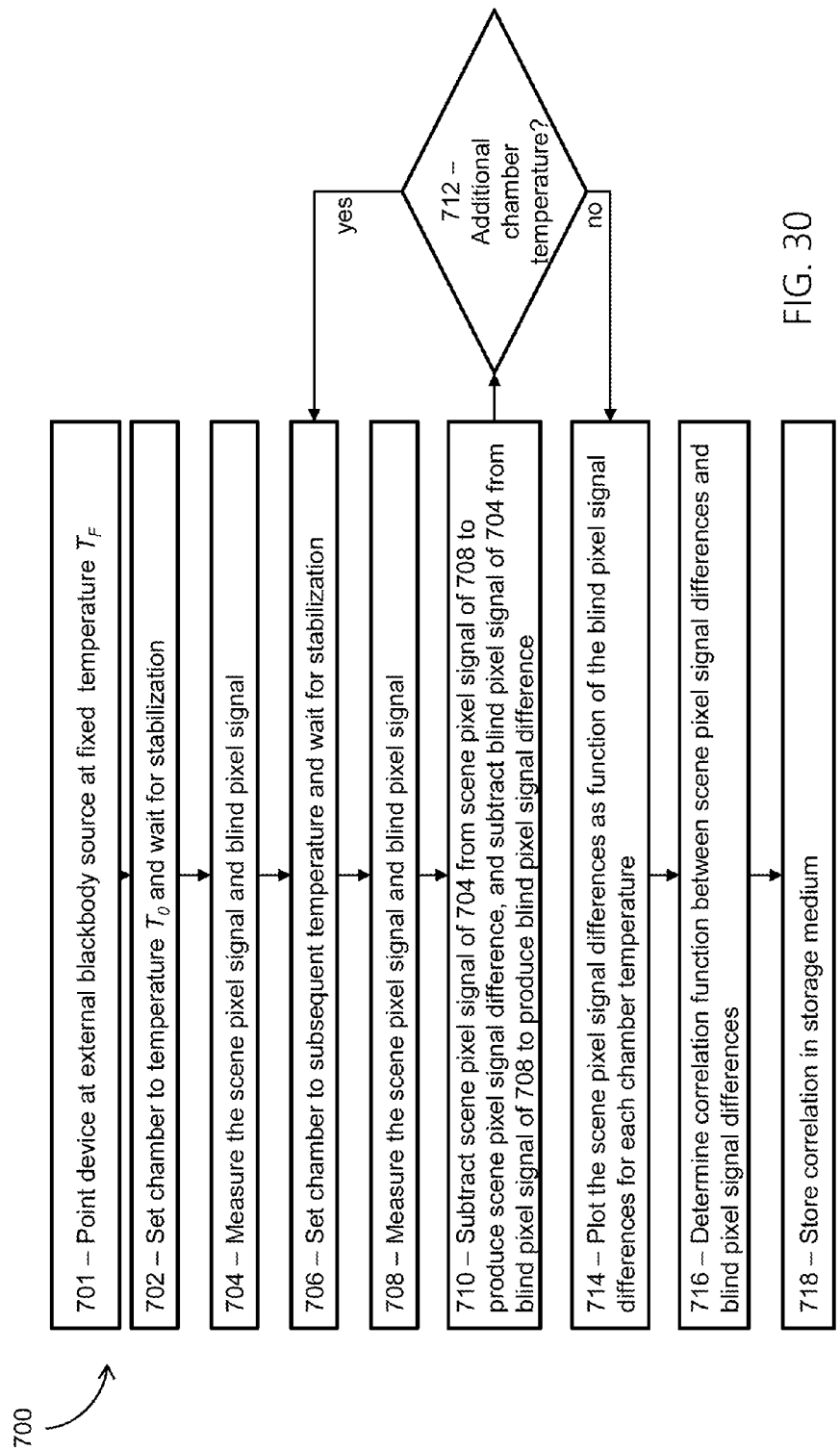
FIG. 30 is a flowchart for determining a correlation according to an embodiment of the invention.

Refer now to FIG. 30, a flowchart of a process 700 for determining a correlation between the drifts of scene pixels signals and the blind pixel signals $S_B$ changes due to changes in environment temperature. Similar to the process 600, before performing the process 700, the device 100-X is placed in the temperature chamber. The device 100-X is also pointed at a source of infrared radiation representing and simulating a scene during the operation of the device 100-X, most conveniently a blackbody source at a known and fixed temperature. The blackbody may be positioned inside the temperature chamber or outside of the temperature chamber and measured by the device 100-X through an infrared transparent window. In the process 700, measurements of the scene pixel signal S and the blind pixel signal $S_B$ are made via the image acquisition electronics 50.

In step 701 (similar to step 601 above), the device 100-X is retained in the temperature chamber and pointed at the external blackbody source which is set to a fixed temperature $T_F$. In step 702, the temperature of the temperature chamber is set to an initial temperature $T_0$. The chamber and the device 100-X are let to stabilize at temperature $T_0$ by waiting an appropriate period of time. In step 704, the imaged pixel signal S and the blind pixel signal $S_B$ are measured after the temperature of the device 100-X reaches stabilization at $T_0$.

In step 706, the temperature of the temperature chamber is set to a new temperature $T_1$, and the external blackbody is maintained at the temperature T. The chamber and the device 100-X are let to stabilize at temperature $T_1$ by waiting an appropriate period of time. In step 708, the scene pixel signal S and the blind pixel signal $S_B$ are measured after the temperature of the device 100-X reaches stabilization at $T_1$.

In step 710, the imaged pixel signal S measured in step 704 is subtracted from the imaged pixel signal S measured in step 708. The result of step 710 yields the temporal drift of the imaged pixel signal due to the change in the temperature of the temperature chamber. Also in step 710, the blind pixel signal $S_B$ measured in step 704 is subtracted from the blind pixel signal $S_B$ measured in step 708.

Similar to the process 600, the process 700 may continue over a range of chamber temperatures of interest, shown by decision step 712. For each newly selected chamber temperature (third, fourth, etc.), the imaged pixel signal S measured in step 704 is subtracted from the imaged pixel signal S measured at the presently selected temperature, and the blind pixel signal $S_B$ measured at step 704 is subtracted from the blind pixel signal $S_B$ measured at the same selected temperature. This procedure can be performed for all the temperatures within the required operating range of the imaging device.

In step 714, the resultant differences in the scene pixels obtained in step 710 are plotted as function of the blind pixel differences obtained at each chamber temperature. In step 716, the correlation function is determined by analyzing the results of the plot obtained in step 714. Numerical methods, such as, for example, curve-fitting, least-squares, or other suitable methods, can be used to further facilitate the determination of the correlation function.

As should be apparent, the resulting correlation function can be interpolated and extrapolated to cover operating temperature ranges not measured during the execution of the processes 600 and 700. In step 718, the correlation function determined in step 716 is stored in a memory coupled to the processor 54, such as, for example, the storage medium 56.

Note that typical environment temperature variations used during the execution of the processes 600 and 700 may depend on various factors such as, for example, the location of the device 100-X when in the operational stage and the intended specific use of the device 100-X when in the operational stage. For example, when the device 100-X is used for monitoring in industrial installations and facilities for gas leakages and/or flame presence, the temperature variations occurring during the execution of the processes 600 and 700 are typically in the range of tens of degrees.

As a result of the correlation function determined by the process 700, during the operation of the device 100-X, signal drifts of the measured scene pixel signals can be compensated for in real time while the temperature of the environment changes. The process of compensating and/or correcting for the signal drifts during operation of the device 100-X is detailed in FIG. 31.

Figure 31:
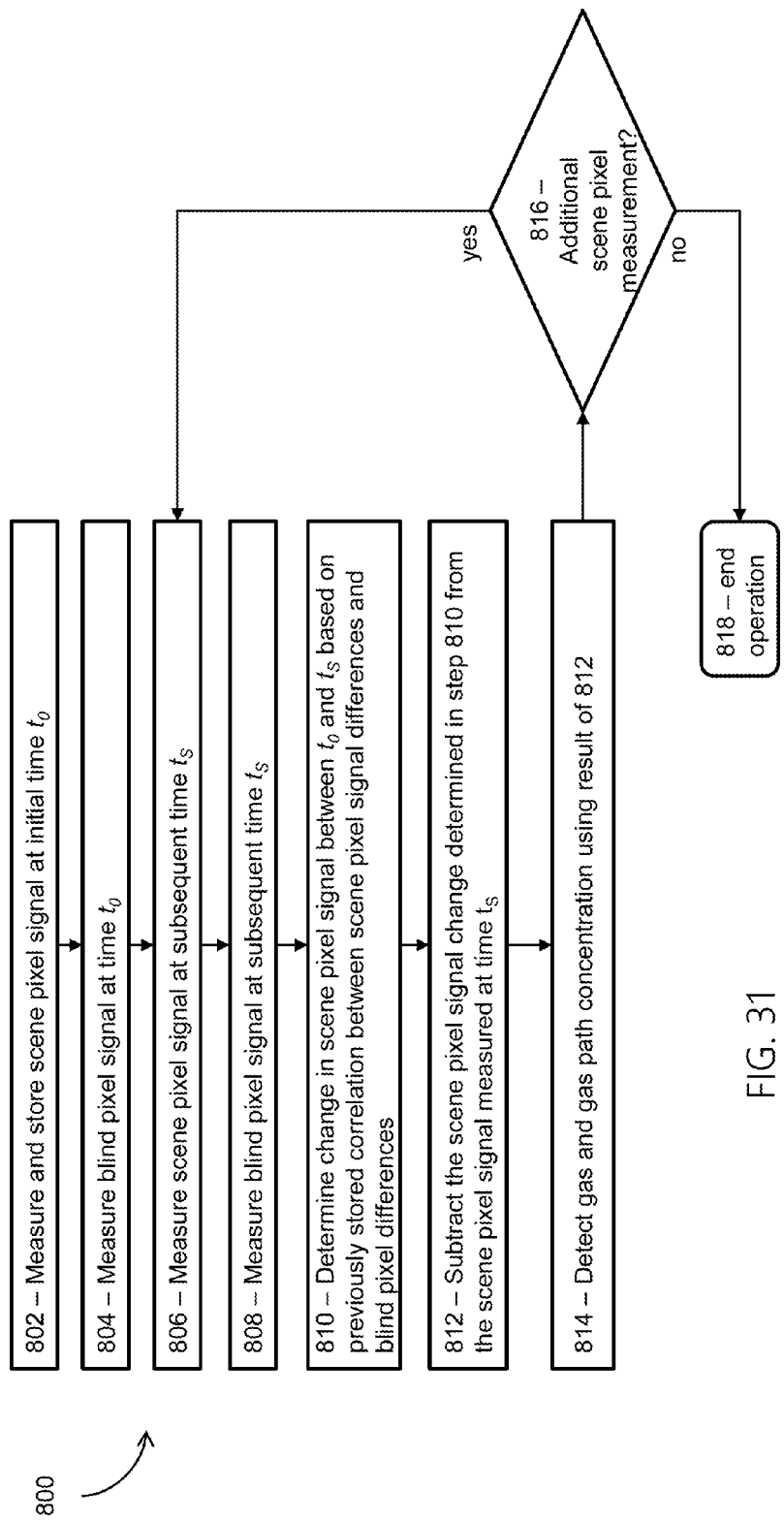
FIG. 31 is flowchart for correcting for drift according to an embodiment of the invention.

Refer now to FIG. 31, a flowchart of a process 800 for correcting for the signal drifts in the imaged pixel signal S caused by environment temperature changes, while the device 100-X is operational in the field. In steps 802-814 the device 100-X is operational in the field and monitors a scene in an industrial environment, automatically and without human intervention.

In step 802, the scene pixel signal S is measured and stored at an initial time $t_0$. The scene pixel measured at time $t_0$ may be stored in the storage medium 56 or stored in a temporary memory coupled to the processor 54. In step 804, the blind pixel signal $S_B$ is measured at the same initial time $t_0$. In step 806, the scene pixel signal S is measured at a subsequent time $t_S$ after the initial time $t_0$. In step 808, the blind pixel signal $S_B$ is measured at the same subsequent time $t_S$.

In step 810, the blind pixel signal $S_B$ measured in step 804 is subtracted from the blind pixel signal $S_B$ measured in step 808. In step 810, the drift of scene pixel signal that occurred between the measurement time $t_0$ and $t_S$ (due to change in the environment temperature) is determined from the correlation function of signal differences determined and stored in the procedure 700. The determination of the drift of scene pixel signal in step 810 is accomplished by subtracting the blind pixel signal measured in step 804 from the blind pixel signal measured in step 808. The resultant difference in blind pixel signal measurements is substituted into the correlation function of signal differences determined in the procedure 700 to determine the drift of scene pixel signal.

In step 812, the scene pixel signal S measured at step 806 is modified by subtracting from it the drift value determined in step 810.

In step 814, the scene pixel signal modified in step 812 is used to assess the presence or absence of the gas of interest and/or flame in the corresponding scene region, and to calculate the gas path concentration distribution if the gas is present, as well as imaging and measuring the gas cloud path concentration distribution and/or flame. As should be apparent, steps 806-814 can be repeated, as needed, for additional measurements by the device 100-X of the scene pixel signals for the detection of the gas and/or flame and path concentration of the gas. This is shown by decision step 816. Accordingly, if additional scene pixel signal measurements are needed, the process 800 returns to step 806 (at a new subsequent time $t_S$). If no additional scene pixel signal measurements are needed, the process ends at step 818.

Note that as a result of the structure and operation of the device 100-X when in the operational stage, the radiation from the blackbody source 60 (or sources in the case of the device 100-2) is projected onto the detector region associated with the blind pixel (i.e., the second detector region 1b of the device 100-2, and the third detector region 1c of the device 100-4) continuously over the duration for which the radiation from the scene is focused onto the detector region(s) not associated with the blind pixels (i.e., the first detector region 1a of the device 100-2, and the two detector regions 1a and 1b of the device 100-4). This is required by the process and results in the reduced frequency of shutter open and closing when in the operational stage, and in a more accurate determination and quantification of the relevant gas present in the scene.

Note that the blind pixel signal that is used to correct the drift in an imaged pixel signal is typically, and preferably, the blind pixel signal associated with the blind pixel that is positioned above or below the associated imaged pixel. In other words, the blind pixel signal used to correct the drift in an imaged pixel signal is preferably the blind pixel signal associated with the detector element closest in position to the detector element associated with the imaged pixel signal. For example, with respect to the device 100-4, as shown in FIG. 28B, the blind pixel 1c-1 is used to correct for the drift in imaged pixel 1b-1. Likewise, the blind pixel 1c-2 is used to correct for the drift in imaged pixel 1a-1. As should be understood, similar techniques can be used for the device 100-2.

As mentioned above, the above described processes 600, 700 and 800 were explained with reference to correcting for the drift in a single imaged pixel signal. As previously mentioned, the same processes may be performed for each of the imaged pixels signals, and may be performed in parallel. The process for correcting for the drift may be supplemented by known methods, such as, for example, NUC, in order to further reduce and correct for the effect of the signal drift. As a result of the drift correction via the processes 600, 700 and 800 described above, the supplemental NUC method is performed at a reduced frequency. The frequency of operation of the supplemental NUC method is typically in the range of once per hour to once per day.

It will be appreciated that the above descriptions are intended only to serve as examples, and that many other embodiments are possible within the scope of the present invention as defined in the appended claims.

What is claimed is:

1. A device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising:
   (a) a detector of the radiation from the scene, the detector including a first and second plurality of detector elements and a filtering arrangement integrated thereon, the filtering arrangement including a first and second plurality of filtering elements, each of the first and second plurality of filtering elements having a respective pass band and stop band, the first wavelength region being within the pass bands of the first plurality of filtering elements and the stop bands of the second plurality of filtering elements and, the second wavelength region being within the pass bands of the second plurality of filtering elements and the stop bands of the first plurality of filtering elements;
   (b) an image forming optical component for forming an image of the scene on the detector, the radiation being imaged simultaneously onto the first and second plurality of detector elements, the imaged radiation on the first plurality of detector elements including radiation in the first wavelength region and the imaged radiation on the second plurality of detector elements including radiation in the second wavelength region; and
   (c) electronic circuitry electronically coupled to the detector, the electronic circuitry configured to:
      (i) produce a pixel signal from each respective detector element, each of the pixel signals including information associated with the absorption or emission of radiation in one of the respective wavelength regions by each of the first and second materials, and
      (ii) determine the presence or absence of the first and second materials based on the produced pixel signals.

2. The device of claim 1, wherein the filtering arrangement is integrated by depositing a substrate on a surface of the detector, the substrate including the first and second plurality of filtering elements.

3. The device of claim 1, wherein the filtering arrangement is integrated by doping the first and second plurality of detector elements, such that the first plurality of detector elements is sensitive to radiation in the first wavelength region, and the second plurality of detector elements is sensitive to radiation in the second wavelength region.

4. The device of claim 1, wherein the first and second plurality of filter elements are arranged such that each filter element of the first plurality of filter elements is adjacent to at least one respective filter element of the second plurality of filter elements.

5. The device of claim 1, wherein the detector includes separate first and second contiguous detector regions, the first detector region including the first plurality of detector elements, and the second detector region including the second plurality of detector elements.

6. The device of claim 1, wherein each filtering element of the first plurality of filtering elements is aligned with a respective detector element of the first plurality of detector elements and, each filtering element of the second plurality of filtering elements is aligned with a respective detector element of the second plurality of detector elements.

7. The device of claim 1, wherein the detector includes a third plurality of detector elements, and the device further comprises:
   (d) a radiation source different from the scene,
   wherein the image forming optical component projects radiation from the radiation source onto the third plurality of detector elements, and wherein the electronic circuitry is further configured to:
      (iii) produce, for each detector element of the third plurality of detector elements, a second pixel signal from the radiation source projected by the image forming optical component onto the third plurality of detector elements, and
(iv) modify each respective pixel signal, produced from the first and second plurality of detector elements, according to a predetermined function to produce a respective modified pixel signal, the predetermined function defining a relationship between a change in a respective second pixel signal and a change in the respective pixel signal, produced from the first and second plurality of detector elements, induced by a changing environment feature.

8. A device for imaging radiation from a scene, the radiation including at least a separate first and second wavelength region, the scene including at least one of a first and second material, the first material having spectral characteristics in the first wavelength region and the second material having spectral characteristics in the second wavelength region, the device comprising:
(a) a detector of the radiation from the scene, the detector including a plurality of detector elements, each detector element including a first and second detector element region, each of the first detector element regions being sensitive to radiation in the first wavelength region and each of the second detector element regions being sensitive to radiation in the second wavelength region;
(b) an image forming optical component for forming an image of the scene on the detector, the radiation being imaged simultaneously onto the plurality of detector elements, such that the imaged radiation on each of the first detector element regions includes radiation in the first wavelength region and the imaged radiation on each of the second detector element regions includes radiation in the second wavelength region; and
(c) an electronic circuitry arrangement electronically coupled to the detector, the electronic circuitry arrangement configured to:
(i) produce a pixel signal from each respective detector element region, each of the pixel signals including information associated with the absorption or emission of radiation in one of the respective wavelength regions by each of the first and second materials, and
(ii) determine the presence or absence of the first and second materials based on the produced pixel signals.

9. The device of claim 8, wherein the electronic circuitry arrangement includes a first and second electronic circuits, the first electronic circuit being electronically coupled to the first detector element regions, and the second electronic circuit being electronically coupled to the second detector element regions, wherein the first electronic circuit is configured to produce a pixel signal from each respective first detector element region, and the second electronic circuit is configured to produce a pixel signal from each respective second detector element region.

10. The device of claim 8, wherein the detector includes a second plurality of detector elements, and the device further comprises:
(d) a radiation source different from the scene, wherein the image forming optical component projects radiation from the radiation source onto the second plurality of detector elements, and wherein the electronic circuitry arrangement is further configured to:
(iii) produce, for each detector element of the second plurality of detector elements, a second pixel signal from the radiation source projected by the image forming optical component onto the second plurality of detector elements, and
(iv) modify each respective pixel signal, produced from the first and second detector element regions, according to a predetermined function to produce a respective modified pixel signal, the predetermined function defining a relationship between a change in the respective second pixel signal and a change in the respective pixel signal, produced from the first and second detector element regions, induced by a changing environment feature.

11. A method for reducing drift induced by at least one changing environment feature when imaging radiation from a scene, the radiation including at least a separate first and second wavelength region, the method comprising:
(a) focusing, over a duration of time, radiation from the scene through an image forming optical component onto a first region of a detector to produce at least a first pixel signal, the image forming optical component being positioned within a first enclosure volume;
(b) positioning a blackbody radiation source proximate to the image forming optical component;
(c) projecting radiation from the blackbody radiation source onto a second region of the detector to produce a second pixel signal, the first and second regions of the detector being non-overlapping regions and, the radiation from the blackbody radiation source being continuously projected onto the second region of the detector over the duration of time for which the radiation from the scene is focused onto the first region of the detector; and
(d) modifying the first pixel signal based in part on a predetermined function to produce a modified pixel signal, the predetermined function defining a relationship between a change in the second pixel signal and a change in the first pixel signal induced by the at least one changing environment feature.

12. The method of claim 11, further comprising:
(e) determining the change in the first pixel signal induced by the changing environment feature based on the predetermined function, and wherein the modified pixel signal is produced by subtracting the determined change in the first pixel signal from the first pixel signal.

13. The method of claim 11, wherein the predetermined function is based on the correlation between the change in the second pixel signal and the change in the first pixel signal induced by the changing environment feature.

14. The method of claim 13, further comprising:
(e) determining the correlation, wherein the determining of the correlation is performed prior to performing (a).

15. The method of claim 13, wherein the detector and the image forming optical component are positioned within a chamber having an adjustable chamber temperature, and a verification of the correlation is determined by:
(i) forming a first set of signals provided by each pixel of the first detector region when imaging the blackbody radiation source at a constant temperature and at a range of different chamber temperatures;
(ii) forming a second set of signals provided by the pixels of the second detector region at each of the different chamber temperatures; and
(iii) verifying a correlation between the first and second sets of signals.

16. The method of claim 13, wherein the detector and the image forming optical component are positioned within a chamber having an adjustable chamber temperature, and a determination of the correlation includes:
(i) measuring a first reading of the first pixel signal at a first chamber temperature and measuring a subsequent reading of the first pixel signal at a subsequent chamber temperature;
(ii) subtracting the first reading of the first pixel signal from the subsequent reading of the first pixel signal to define a first set; and
(iii) measuring a first reading of the second pixel signal at the first chamber temperature, measuring a subsequent reading of the second pixel signal at the subsequent chamber temperature and subtracting the first reading from the second reading to define a second set.

17. The method of claim 16, wherein the modifying of the first pixel signal includes:
(i) measuring a first reading of the first pixel signal at a first time instance and measuring a subsequent reading of the first pixel signal at a subsequent time instance;
(ii) measuring a first reading of the second pixel signal at the first time instance and measuring a subsequent reading of the second pixel signal at the subsequent time instance; and
(iii) subtracting the first reading of the second pixel signal from the subsequent reading of the second pixel signal to define a third set.

18. The method of claim 11, wherein the at least one environment feature includes environment temperature.

19. The method of claim 11, wherein the blackbody radiation source is positioned within the first enclosure volume.

20. The method of claim 11, wherein the blackbody radiation source is positioned at an intermediate focal plane between the image forming optical component and a second optical component for directing radiation from the scene towards the detector.

* * * * *